(12) United States Patent
Kong et al.

(10) Patent No.: US 12,280,492 B2
(45) Date of Patent: Apr. 22, 2025

(54) ELECTROTHERMAL MANIPULATOR

(71) Applicants: The Board of Trustees of the University of Illinois, Urbana, IL (US); Purdue Research Foundation, West Lafayette, IN (US)

(72) Inventors: Hyunjoon Kong, Urbana, IL (US); Byoungsoo Kim, Urbana, IL (US); Jonghwi Lee, Urbana, IL (US); Chi Hwan Lee, West Lafayette, IN (US); Min Ku Kim, Lafayette, IN (US)

(73) Assignees: The Board of Trustees of the University of Illinois, Urbana, IL (US); Purdue Research Foundation, West Lafayette, IN (US)

( * ) Notice: Subject to any disclaimer, the term of this patent is extended or adjusted under 35 U.S.C. 154(b) by 821 days.

(21) Appl. No.: 17/462,862

(22) Filed: Aug. 31, 2021

(65) Prior Publication Data
US 2022/0063110 A1    Mar. 3, 2022

Related U.S. Application Data

(60) Provisional application No. 63/072,634, filed on Aug. 31, 2020.

(51) Int. Cl.
*B25J 15/00* (2006.01)
*B25J 7/00* (2006.01)
(Continued)

(52) U.S. Cl.
CPC ............... *B25J 15/008* (2013.01); *B25J 7/00* (2013.01); *B25J 11/0095* (2013.01); *B25J 19/0025* (2013.01)

(58) Field of Classification Search
CPC ........ B25J 15/008; B25J 7/00; B25J 11/0095; B25J 19/0025; A61B 34/00;
(Continued)

(56) References Cited

U.S. PATENT DOCUMENTS 6,521,187 B1 * 2/2003 Papen .................. G01F 1/48
73/863.02
6,575,020 B1 * 6/2003 de Charmoy Grey .................
G01N 9/002
73/54.23

(Continued)

OTHER PUBLICATIONS

Bai et al. (2013) "Thermoresponsive composite hydrogels with aligned macroporous structure by ice-templated assembly," Chem. Mater. 25, 4551-4556.

(Continued)

*Primary Examiner* — Stephen A Vu
(74) *Attorney, Agent, or Firm* — Leydig, Voit & Mayer, Ltd.

(57) ABSTRACT

Provided herein are manipulators for handling fragile layers and related methods of handling using the manipulators. The manipulators comprise a contact surface with thermally responsive recess features and a microelectric heater in thermal contact with the contact surface. In this manner, the manipulator is an electrothermal manipulator, with changes in temperature providing a contact force to pick-up a transferable layer material and a release force to facilitate release of the transferable from the manipulator.

20 Claims, 41 Drawing Sheets

(51) Int. Cl.
*B25J 11/00* (2006.01)
*B25J 19/00* (2006.01)

(58) Field of Classification Search
CPC .... A61B 2017/00969; H01L 21/67103; H01L 21/67132; H01L 21/68707
See application file for complete search history.

(56) References Cited

U.S. PATENT DOCUMENTS

| | | | | |
|---|---|---|---|---|
| 6,720,710 | B1* | 4/2004 | Wenzel | F04B 43/046 417/474 |
| 8,079,278 | B2* | 12/2011 | Xi | B81C 99/002 73/863.02 |
| 8,861,171 | B2 | 10/2014 | Prahlad et al. | |
| 2004/0195851 | A1* | 10/2004 | Hayashi | B81C 99/002 294/64.3 |
| 2008/0119842 | A1 | 5/2008 | Palanker et al. | |
| 2017/0239927 | A1 | 8/2017 | White et al. | |

OTHER PUBLICATIONS

Baik et al. (2017) "A wet-tolerant adhesive patch inspired by protuberances in suction cups of octopi," Nature. 546, 396-400.
Carlson et al. (2012) "Transfer Printing Techniques for Materials Assembly and Micro/Nanodevice Fabrication," Adv. Mater. 24, 5284-5318.
Choi et al. (2016) "Cephalopod-Inspired Miniaturized Suction Cups for Smart Medical Skin," Adv. Healthc. Mater. 5, 80-87.
De et al. (2007) "Assessment of Tissue Damage due to Mechanical Stresses," Int. J. Rob. Res. 26, 1159-1171.
Gao et al. (1995) "Diffusion in HPMC Gels. II. Prediction of Drug Release Rates from Hydrophilic Matrix Extended-Release Dosage Forms," Pharm. Res. 12, 965-971.
Han et al. (2016) "Mechanically Reinforced Skin-Electronics with Networked Nanocomposite Elastomer," Adv. Mater. 28, 10257-10265.
Jeong et al. (2013) "Materials and Optimized Designs for Human-Machine Interfaces via Epidermal Electronics," Adv. Mater. 25, 6839-6846.
Jeong et al. (2014) "Capacitive epidermal electronics for electrically safe, long-term electrophysiological measurements," Adv. Healthc. Mater. 3, 642-648.
Kier et al. (2002) "The structure and adhesive mechanism of octopus suckers," Integr. Comp. Biol. 42, 1146-1153.
Kim et al. (2011) "Epidermal Electronics," Science. 333, 838-843.
Kim et al. (2012) "Electronic sensor and actuator webs for large-area complex geometry cardiac mapping and therapy," Proc. Natl. Acad. Sci. 109, 19910-19915.
Kim et al. (2017) "3D Cocontinuous Composites of Hydrophilic and Hydrophobic Soft Materials: High Modulus and Fast Actuation Time," ACS Macro Lett. 6, 1119-1123.
Kim et al. (Oct. 2020) "Electrothermal soft manipulator enabling safe transport and handling of thin cell/tissue sheets and bioelectronic devices." Science Advances, vol. 6, No. 42, eabc5630. DOI: 10.1126/sciadv.abc5630.
Lee et al. (2016) "Octopus-Inspired Smart Adhesive Pads for Transfer Printing of Semiconducting Nanomembranes," Adv. Mater. 28, 7457-7465.
Liang et al. (2011) "Toward Clean and Crackless Transfer of Graphene," ACS Nano. 5, 9144-9153.
Nishida et al. (2004) "Functional bioengineered corneal epithellial sheet grafts from corneal stem cells expanded ex vivo on a temperature-responsive cell culture surface," Transplantation. 77, 379-385.
Prabhasawat et al. (2016) "Long-term result of autologous cultivated oral mucosal epithelial transplantation for severe ocular surface disease," Cell Tissue Bank. 17, 491-503.
Sekine et al. (2013) "In vitro fabrication of functional three-dimensional tissues with perfusable blood vessels," Nat. Commun. 4, 1399.
Tananuvat et al. (2017) "Limbal stem cell and oral mucosal epithelial transplantation from ex vivo cultivation in LSCD-induced rabbits: histology and immunologic study of the transplant epithelial sheet," Int. Ophthalmol. 37, 1289-1298.
Tian et al. (Mar. 2019) "Large-area MRI-compatible epidermal electronic interfaces for prosthetic control and cognitive monitoring," Nat. Biomed. Eng. 3, 194-205.
Tramacere et al. (2013) "The Morphology and Adhesion Mechanism of Octopus vulgaris Suckers," PLoS One. 8, e65074.
Wang et al. (2011) "Spatial light interference microscopy (SLIM)," Opt. Express. 19, 1016-1026.
Wirthl et al. (2017) "Instant tough bonding of hydrogels for soft machines and electronics," Sci. Adv. 3:e1700053.
Yan et al. (2017) "Thermal Release Transfer Printing for Stretchable Conformal Bioelectronics," Adv. Sci. 4, 1700251.
Yang et al. (2005) "Cell sheet engineering: Recreating tissues without biodegradable scaffolds," Biomaterials. 26, 6415-6422.
Yang et al. (2007) "Reconstruction of functional tissues with cell sheet engineering," Biomaterials. 28, 5033-5043.

* cited by examiner

Reference    Ground    Measurement

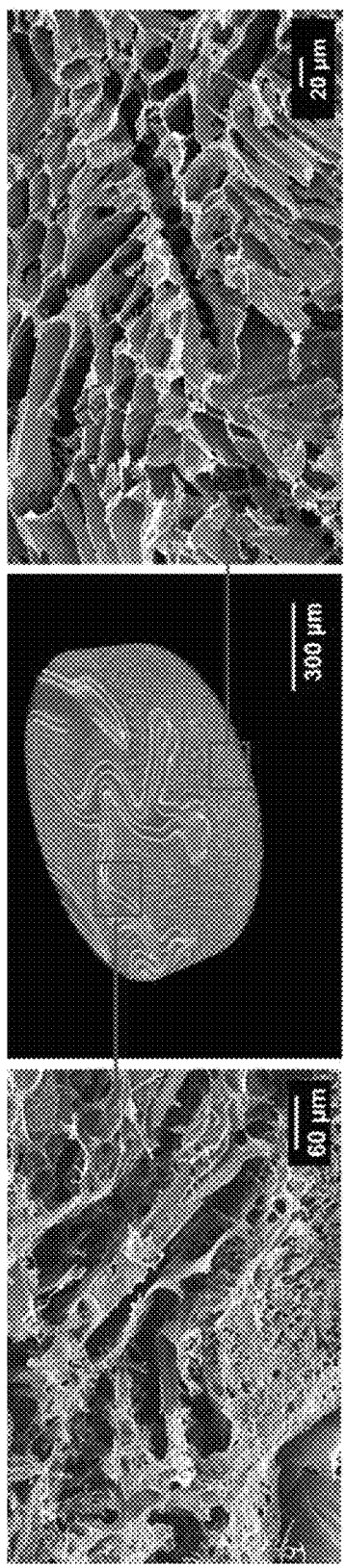

ELECTROTHERMAL MANIPULATOR

CROSS-REFERENCE TO RELATED APPLICATIONS

This application claims the benefit of priority to U.S. Provisional Patent Application No. 63/072,634 filed Aug. 31, 2020 which is hereby incorporated by reference in its entirety.

STATEMENT REGARDING FEDERALLY SPONSORED RESEARCH OR DEVELOPMENT

This invention was made with government support under Award Numbers CBET-0939511 and CBET-1932192 awarded by the National Science Foundation, Award Number 1R21 HL109192 awarded by National Institutes of Health, and Award Number W81XWH-17-1-022 awarded by the Department of Defense Vision Research Program. The government has certain rights in the invention.

BACKGROUND

The systems and methods provided herein generally relate to transfer of thin and fragile materials.

Thin materials often need to be handled for transport and assembly but are easily damaged by external forces, resulting in unwanted deformation, wrinkling and/or tears, with resultant adverse impact on material function and usefulness. Examples of such materials include cell-sheets and tissue layers, that are often used in the medical setting and have been shown to have greater efficacy than individual cells. Similarly, ultrathin electronic films used for sensors, chips, and capacitance layering, also have fragility concerns that impact the ability to reliably handle, including in the transfer process from a donor substrate to a receiving substrate.

Conventional systems for handling thin materials include use of forceps or suction cups. Forceps, however, suffer from the problem of exerting unreliable and relatively larger forces, including at the point of contact with the layer, with an attendant high risk of damage. Similarly, conventional suction cups tend to require relatively high pressures to reliably pick-up a material layer, that result in a high-risk of damage. In addition, the suction cup techniques must be performed under water.

There is a need in the art for manipulators that can reliably manipulate fragile and thin materials without compromising the material integrity or damaging the underlying material components and function by providing minimal pressures and that are able to function under wet or dry conditions. These problems are addressed herein by use of specially configured manipulators having a thermally-active and soft contact layer that reliably, quickly and efficiently provides gentle and uniform contact pressure changes over a relatively large surface area, thereby achieving rapid pick-up and release of fragile thin layers of material that is reliable and without damage.

SUMMARY

Provided herein are manipulators that are able to handle thin and fragile layers and films, including biological tissues. The manipulators are particularly suited for application of layers such as cell-sheets, medical films, and ultra-thin electronic materials. The ability to apply such layers, involving layer pick-up, movement and release, to an application surface, is challenging due to the fragility of those layers, resulting in a high-risk of damage, such as tearing, during any one or more steps of lift-off from a donor substrate, subsequent movement and release to an application surface. The manipulator systems and related methods provided herein can transfer materials in wet conditions and in dry conditions, while also reducing transfer time. Accordingly, the systems are particularly suited for biomedical applications related to tissue and/or cell sheet transfers, as well as for handling of ultra-thin electronic materials.

The manipulators provided herein rely on an elegant air-trap technique to generate controllable pressures against the manipulated surface by changes in temperature. In particular, a thermally-responsive contact layer having recess features (including aligned micro channels) on a contact surface, is connected to an electronic heater. The heater causes changes in the size of the recess features, with resultant pressure changes when the contact layer is in contact with a manipulated surface of a transferable layer. For example, the contact layer may comprise a hydrogel, where the temperature increase drives water out of the contact layer, resulting in deformation and contraction, with attendant decrease in size of the recess features, including at or near the contact surface of the contact layer. Decreasing the temperature can then restore water into the contact layer, increasing or relaxing the recess features back to the original size, or at least a size greater than the corresponding size at a higher temperature. This accordingly "cycles" the pressure in the recess features from an adhesive pressure or force for layer pick-up by the manipulator to a release pressure or force for layer removal from the manipulator. In this manner, a thin, fragile layer can be picked-up by the manipulator, moved and released.

In an embodiment, the manipulator comprises: a contact layer having a contact surface with thermally responsive recess features; a microelectric heater in thermal contact with the contact surface; and an electrical power source electrically connected to the microelectric heater. The thermally responsive recess features are configured to generate differential pressures between a thermally-actuated and a thermally-relaxed state by changing in effective volume when in contact with the manipulated surface. In particular, after contact an increase in effective volume of the recess features effectively decreases the pressure, thereby exerting an adhesive force against the manipulated surface. Accordingly, the thermally responsive recess features have a thermally actuated geometry with microelectric heater actuation and a thermally relaxed geometry without microelectric heater actuation, wherein the thermally actuated geometry is different than the thermally relaxed geometry. The geometry may correspond to an effective volume of the recess features, so that the change in volume correspondingly changes the pressure in the recess feature exerted against the manipulated surface, thereby changing the adhesion force from an adhesion force sufficiently high to pick up and reliably hold the transferable layer, to an adhesion force that is sufficiently low to release the transferable layer, including a negative adhesion force that corresponds to a slight force that can actively overcome any surface tension to force the transferable surface away from the manipulator contact surface.

The contact layer may comprise a polymeric hydrogel or an elastomer.

The contact layer may be soft with an anisotropic elastic modulus less than or equal to 10 kPa, with the elastic modulus in a direction perpendicular to an alignment direction of the recess features that is 1.5 to 2.5 times lower than the elastic modulus in a direction parallel to the alignment direction of the recess features; has an average thickness that is greater than or equal to 100 µm and less than or equal to 1 cm; has a footprint (effective surface area corresponding to a contact area between the contact surface and the transferable material defined by the outermost contact perimeter between the contact surface and the transferable layer) that is greater than or equal to 10 mm² and less than or equal to 350 cm²; has a thermal responsivity that is equal to or less than 10 seconds; has a recess feature porosity of between 90% and 98%; and/or has recess features that are aligned microchannels with an average channel diameter of between 0.1 µm and 500 µm.

The manipulator may further comprise an adhesive layer positioned between the contact layer and the microelectric layer to adhere the contact layer to the microelectric layer. Preferably, the adhesive permits thermal communication between the microelectric layer and the contact layer, thereby minimizing adverse impact on thermal responsivity of the contact layer upon actuation change-of-state.

The thermally responsive recess features may comprise anisotropically aligned microchannels, including anisotropically aligned microchannels that are characterized by an average diameter. For example, the thermally actuated geometry may have an average contracted diameter ($D_A$) and the thermally relaxed geometry may have an average relaxed diameter ($D_R$). In this manner, the change in diameters correspond to a change in volume, thereby effecting a change in contact pressure and, therefore, contact force (e.g., Force=Pressure/Area of Contact). Useful ratios for generating suitable adhesive pressure or forces include, $0.2 \leq D_A/D_R \leq 0.98$.

Depending on the application of interest, suitable adhesive forces are selected. For example, the recess features, including $D_A$ and $D_R$, may be configured to generate a contact pressure with a manipulated surface that is between 0.1 Pa and 500 Pa per recess feature; and/or between 1 kPa and 100 kPa over the entire contact surface in physical contact with the manipulated surface.

Similarly, $D_A$ and $D_R$ may be selected to generate a contact force with a manipulated surface that is between 0.5 mN and 500 N.

The manipulators provided herein are compatible with a range of manipulated surfaces. Exemplary manipulated surfaces include, but are not limited to, a thin biological tissue; an ultrathin electronic film; a fragile inorganic film or membrane; or a thin semiconductor layer.

Depending on the desired adhesive force, response time, and the like, the recess features may have, for a thermally relaxed geometry: an average lineal density of between 1 and 500 recess features per mm; a depth of between 10 µm and 3 cm, including a depth corresponding to a thickness of the capture layer for a microchannel recess feature; a characteristic dimension, including a diameter, a length and/or a width, independently selected from between 10 µm and 3 cm; and/or a recess feature wall thickness of between 0.1 µm and 10 µm.

The microelectric heater may comprise a flexible pattern of resistive wires embedded in or supported by a polymer layer, and optionally a barrier layer to prevent oxidation of the resistive wires, having a total microelectric heater thickness less than or equal to 50 µm. The barrier layer may be a chemically inert layer that is impermeable to air and that does not adversely impact the thermal connectivity with the contact layer. Examples include inert polymer and elastomer layers.

The electrical power source may provide an actuation voltage to the microelectric heater of between 0.1 V to 10 V to actuate the microelectric heater and generate an actuated temperature at the contact surface of between 30° C. and 40° C. within 10 seconds of actuation of the electrical power source.

Upon removal of the actuation voltage, the actuated temperature relaxes to a relaxed temperature, including a room temperature or surrounding ambient temperature, within 5 seconds.

The contact layer may have a thermal conductivity of between 0.1° C./mm*s and 0.6° C./mm*s.

The manipulator may further comprise a support substrate connected to the microelectric heater. This is particularly useful in embodiments where the microelectric heater is itself flexible in order to ensure a reliable and robust thermal contact with the manipulator contact layer.

Also provided herein are methods of handling a transferable layer. In this aspect, "handling" is used broadly to refer to the manipulation of a material, including pick-up from a surface, movement, and deposition, including in a manner analogous to transfer printing. The handling may be used to build a multi-layer device, including a biomedical device having thin, fragile layers. The handling may be a more straightforward process related to deposition of a thin, fragile material to a desired surface.

The method of handling a transferable layer, including a to-be-manipulated surface, may comprise the steps of providing any of the manipulators described herein and energizing the power source to thermally actuate the microelectric heater and provide the thermally responsive recess features in the thermally actuated geometry. The contact surface is brought into contact with the transferable layer and the thermally responsive recess features relaxed toward or to the thermally relaxed geometry by removing or reducing the energizing step to generate an adhesive pressure in the recess features. The transferable layer is lifted and removed by moving the contact layer of the manipulator, thereby handling the transferable layer.

The method may further comprise the step of tuning the contact pressure to a material property of the transferable layer to reduce risk of damage to the transferable layer.

The transferable layer may be a mechanically fragile ultra-thin layer. The transferable layer may be a biomaterial comprising living cells or an ultrathin electronic film.

The method may further comprise the steps of increasing a temperature of the contact layer to provide the thermally responsive recess features in the thermally actuated state and releasing the transferable layer from the contact surface having the thermally responsive recess features in the thermally actuated state.

Also provided are methods of making any of the manipulators provided herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A is a schematic illustration of the soft, electrothermally controlled manipulator and FIG. 1B summarizes a process to transport a thin material using the soft manipulator.

FIG. 2A is a schematic illustrating the fabrication process of the gel with anisotropically aligned microchannels. The gel is prepared by directional crystallization and subsequent polymerization. FIG. 2B is a photograph of the resulting microchanneled hydrogel after swelling in water. FIG. 2C: Microstructure of the gel: left panel is a scanning electron microscopy (SEM) micrograph of the top surface, middle panel is 3-dimensional imaging of the micro-channeled hydrogel via micro-computed tomography (micro-CT), and the right panel is a SEM micrograph of microchannels that connect the top and bottom of the gel. FIG. 2D: Equilibrium swelling ratio of gels at different temperatures. FIG. 2E: The compressive elastic moduli of gels. Samples are compressed in parallel with microchannel direction (axial compression) and perpendicular to microchannel direction (radial compression). FIG. 2F: Time-dependence volumetric changes of micro-channeled gel on heating (25° C. to 40° C.) and cooling (40° C. to 25° C.). The samples are placed on 40° C. or 25° C. plate. The resulting volumetric change is recorded. FIG. 2G: Effective diffusion coefficient of water in gels quantified by the re-swelling plot (FIG. 2F 40° C. to 25° C.). * represents the statistical significance of the difference of values between conditions indicated with line (*p<0.01).

FIG. 3A: Photograph (top panel) and a thermal image of the flexible heater captured using an infrared camera (bottom panel). FIG. 3B: Temperature change over time at differently applied voltages. The temperature profiles of the heater were obtained using an infrared camera. FIG. 3C: Structural configuration of the soft manipulator (left) and a photograph of the soft manipulator (right). FIG. 3D: snapshots of the microchanneled gel in the soft manipulator when the heater was turned on. FIG. 3E: snapshots of the microchanneled gel in the soft manipulator when the heater was turned off. Optical microscopic images illustrate the gel surface when the heater is turned on and off. When the heater is turned on, aligned microchannels of the gel pushed water out while being closed for 20 seconds (FIG. 3D). When the heater is switched off, the gel in the soft manipulator opened microchannels and pulled water back into microchannels within 20 seconds (FIG. 3E). The scale bar represents 100 μm.

FIG. 4A: Snapshots showing the transport of a 4-inch diameter silicon wafer using a soft manipulator (upper images). Schematic illustrating the shrinkage and expansion of microchannels and subsequent water movement in microchannels controlled by the electrothermal signal (lower images). The operating power of the soft manipulator was 5 W. FIG. 4B: The time-dependent variation of normal adhesion strength measured by the dynamic mechanical analyzer (DMA) during the stage 2 and 3 in (FIG. 4A). An initial contact strength of 0.05 kPa was applied to the soft manipulator for this measurement. FIG. 4C: Fluorescence images of water in microchannels of the gel. The image was obtained from a 3D z-stack confocal microscope before (top image) and after adhesion (bottom image) of the soft manipulator to a target surface. The heater was attached to the upper part of the gel. FIG. 4D: Dependency of the adhesion strengths on the initial load. FIG. 4E: Variation in the adhesion strength as a function of cycle number. FIG. 4F: The adhesion strength of the soft manipulator measured with the various target substrates in water and air. An initial contact strength of 0.5 kPa was applied to the soft manipulator using DMA for this measurement.

FIG. 5A: Snapshots of a process to pick up a skeletal myoblast sheet with forceps. The cell sheet was deformed when picking up the sheet using forceps (right). The cell sheet was stained with methylene blue for visualization. FIG. 5B: A snapshot of a process to transport the skeletal myoblast sheet onto a glass surface using the soft manipulator. FIG. 5C: The spatial light interference microscopy (SLIM) images of the cell sheet before (left) and after (right) the transfer, showing off-axis diffraction of the cell sheet. FIG. 5D: A fluorescence image of a multi-layered cell sheet consisting of three different myoblast sheets. The multi-layered sheet was prepared by stacking cell sheets using the soft manipulator. FIG. 5E: Snapshots of a process to transport a skeletal myoblast sheet onto a muscle tissue. It took 30 seconds for the entire transfer process. FIG. 5F: Photographs of a rat eye before and after transplantation of a stem cell sheet. The cell sheet transplanted to the corneal epithelium of a rat eye using the soft manipulator. It took 30 seconds for the entire transfer process. FIG. 5G: Histological examination of the rat eye before (left) and after (right) a stem cell sheet transfer. H&E staining revealed that the stem cell sheet was able to be successfully transplanted onto the anterior corneal surface without substantial interface space generation.

FIG. 6A: Device configuration of the ultrathin EP sensor (t=1 μm) tailored for the measurement of ECG signals. FIG. 6B: A snapshot of a process to transport the device to the surface of the pig heart. It took 30 seconds to capture and deliver the device onto the pig heart. FIG. 6C: A photograph of the device transplanted to the pig heart using the soft manipulator. FIG. 6D: Representative ECG signals measured using the transplanted device.

FIG. 7A-7C: Microstructure analysis of the gel with randomly oriented microchannels: FIG. 7A: scanning electron microscopy (SEM) micrograph of the top surface, FIG. 7B: 3-dimensional imaging of the hydrogel via micro-computed tomography (micro-CT), and FIG. 7C: cross-sectional SEM image. Freeze-dried samples were used for imaging.

FIGS. 8A-8B: SEM micrographs of the top-view (FIG. 8A) and lateral view of anisotropically aligned microchannels (FIG. 8B) of the gel at 25° C. FIGS. 8C-8D, SEM micrographs of the top-view (FIG. 8C) and lateral view of anisotropically aligned microchannels (FIG. 8D) in the gel after shrinkage. The shrinkage was induced by increasing temperature (40° C.), as indicated by the arrow.

FIGS. 9A-9B: SEM micrographs of the top-view (FIG. 9A) and lateral view of randomly oriented microchannels (FIG. 9B) of the gel at 25° C. FIGS. 9C-9D, SEM micrographs of the top-view (FIG. 9C) and lateral view of randomly oriented microchannels (FIG. 9D) in the gel after shrinkage. The shrinkage was induced by increasing temperature (40° C.) as indicated by the arrow.

FIG. 11A: Snapshots show the heat propagation through the gel, which is attached to a heater. The activation temperature of the heater was 40° C. The gel used in this example is microchanneled PNIPAAm gel. FIG. 11B: A thermal image showing regions of interest. FIG. 11C: Temperature of the gel versus time. The diameter and thickness of the gel used in this analysis are 30 and 2 mm, respectively.

FIG. 14A: Schematic illustration of the set-up that measures the normal adhesion strength in the water of varying temperatures. The gel layer of the soft manipulator was pre-heated by the heater and brought into contact with a 4-inch diameter silicon wafer immersed in a water bath. The temperature of the water bath was controlled by a digital circulator. Then, the heater of the soft manipulator was turned off. The adhesion strength was measured by a DMA. FIG. 14B: The adhesion strength of the soft manipulator measured at different temperatures of water.

FIG. 15A: Schematic illustration of measurement of the normal pressure development under different initial contact pressures. The gel layer of the soft manipulator was pre-heated by the heater and brought into contact with a 4-inch diameter silicon wafer. DMA controlled the initial contact pressure of the gel layer onto the silicon wafer. Then, the heater of the soft manipulator was turned off to expand the gel layer. FIG. 15B: The normal pressure developed by the soft manipulator varies with the initial contact pressure.

FIG. 16A: Elastic modulus of the alginate hydrogels prepared by cross-linking reaction between uronic acid of alginate and adipic acid dihydrazide (AAD). 0.05 and 0.2 represent the molar ratio between AAD and uronic acids of alginate (MAAD). FIG. 16B: The normal pressure development of the soft manipulator against different target materials. An initial contact strength of 0.25 kPa was applied to the soft manipulator for this measurement.

FIG. 18A: Representative confocal images of the live-dead assay for the cell sheet before (left) and after (right) transport. Green color represents live cells, and the red color represents dead cells. FIG. 18B: Quantification of live cells using the images in FIG. 18A.

FIG. 21A: Preprogrammed ECG signals generated using a waveform generator. FIG. 21B: The measured ECG signals using the transplanted sensor on the surface of the pig heart.

DETAILED DESCRIPTION

Figure 1A:
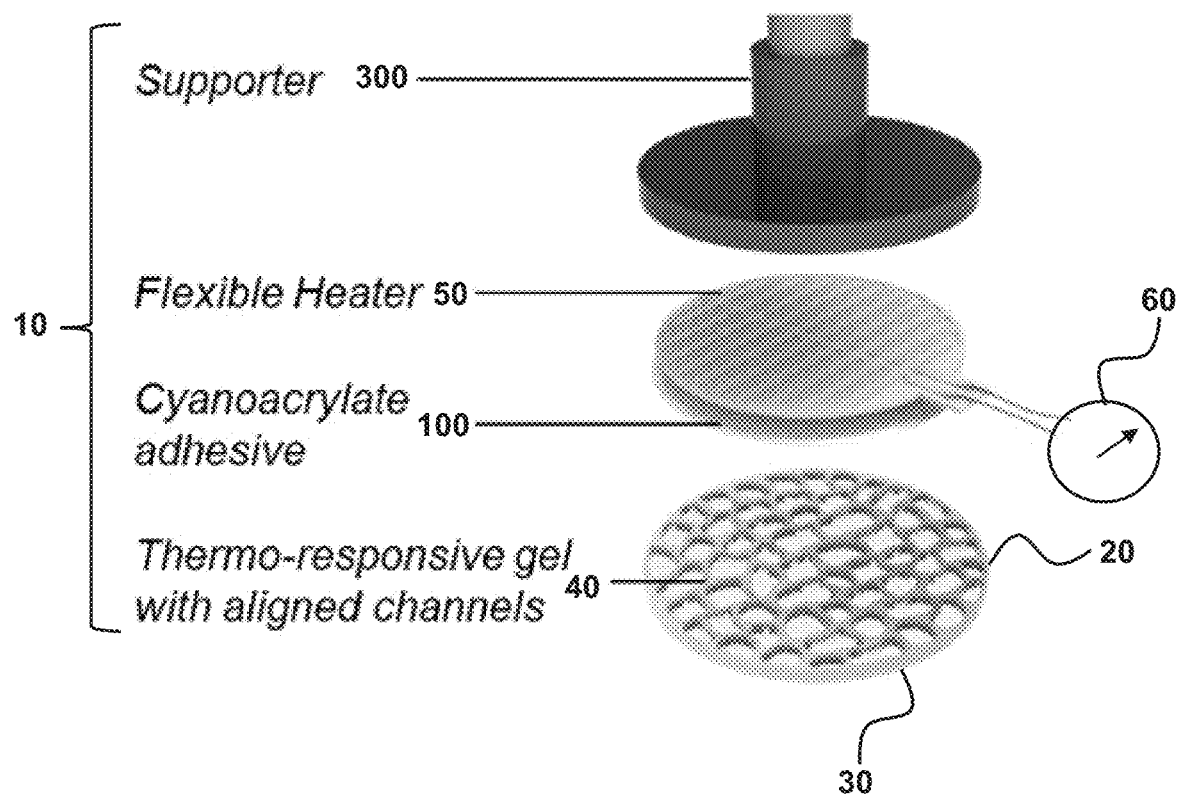
FIG. 1A-1B: Design of the electrothermal soft manipulator for delicate material transport.

In the following description, numerous specific details of the devices, device components and methods of the present invention are set forth in order to provide a thorough explanation of the precise nature of the invention. It will be apparent, however, to those of skill in the art that the invention can be practiced without these specific details. In general, the terms and phrases used herein have their art-recognized meaning, which can be found by reference to standard texts, journal references and contexts known to those skilled in the art. The following definitions are provided to clarify their specific use in the context of the invention.

The term "recess features" refers to those portions of the contact layer having spaces, passages, or void volumes relative to a contact surface of the contact layer. In this manner, the contact layer can be brought into physical contact with a transferable material (also referred herein as a "manipulated surface"), wherein the portion of the contact surface forming side walls of the recess features are in physical contact with the transferable material and the recess features each have a defined volume defined by the transferable material surface that effectively covers and encloses recess features. By manipulating the volume of the recess features, a pressure change occurs in each of the recess features. In this manner, the pressure may be provided to generate a contact force sufficient to lift and move the transferable material with the manipulator by "expanding" the recess features, thereby decreasing pressure in the recess features. Then, when the transferable material is to be released from the manipulator, the volume may be relaxed back to a lower volume (e.g., by "contracting" the recess features), thereby increasing pressure in the recess features, so that the transferable material is gently released from the manipulator.

Accordingly, a "thermally responsive recess feature" refers to a recess feature whose geometry, including size or volume, is dependent on temperature.

"Contact layer" refers to a material that is thermally active. For example, the contact layer may be a polymeric hydrogel, including, but not limited to, polyacrylamide, poly(N-isopropylacrylamide), poly(ethylene glycol) diacrylate/dimethacrylate, alginate, Pluronic, gelatin, agarose. The contact layer may be any polymer that can hybridize with poly(N-isopropylacrylamide). The contact later may be an elastomer, such as latex, polyurethanes, silicones, and combinations thereof. The systems and methods provided herein are compatible with any temperature-responsive polymers that undergoes reversible phase transition at a temperature (e.g., including between about 30° C. and 40° C.) from a swollen hydrated state to a shrunken dehydrated state. The movement of water correspondingly changes the geometry or size of the thermally responsive recess feature.

"Soft" refers to an elastic modulus, such as a Young's modulus (stress/strain) so that there is gentle contact between the contact surface and a transferable surface to avoid and minimize risk of damage to the transferable surface. For example, the contact layer may be characterized as having an elastic modulus that is less than or equal to 1 MPa, 100 kPa, or 10 kPa. The elastic modulus may be informed by the application of interest, including the transferable material, and the fragility of the transferable material. As desired, the lower the elasticity of the transferable surface, the lower the elasticity of the contact surface, including for applications where unwanted deformation in the transferable surface is desired.

"Biological layer" refers to a layer of material containing biological material arranged in a thin layer, including less than 1 mm, less than 500 µm, less than 100 µm, or even as thin as a single layer of living biological cells. Biological layer may also refer to a thin matrix layer upon which biological cells and tissue grow. In this manner, a thin substrate layer may be reliably handled and brought into contact with a biological system, such a tissue culture, in a manner that maintains substrate geometry, avoids folding or tearing.

"Ultrathin electronic film" refers to electronically-relevant containing layers having a thickness less than 100 µm, less than 10 µm or less than 1 µm, including between 1 nm and 1 µm. The films may comprise patterned layers of inorganic materials, metals, semiconductors and the like, useful in manufacture of electronic devices. "Thin" refers to layers having a thickness less than about 5 mm, or less than 1 mm, including between 1 µm and 1 mm.

"Fragile" refers to a material that would tend to experience a functional failure during conventional handling processes. The manipulators and methods provided herein provide gentle contact and release forces that ensures the fragile material remains functional and not degraded. Various parameters known in the art can be used to define whether a material is fragile, including brittleness, yield strength, bending modulus. For electronics applications, the material fails with very small deformation, such as a strain that is less than 1% or less than 0.5%. In the context of biological applications, fragile refers to a material that is easily damaged with minimal force application, or localized regions having a high stress gradient. Fragile may be described in terms of a quantifiable parameter, such as an elastic modulus. For example, the elastic modulus may be a Young's modulus that is greater than or equal to 0.1 kPa and less than or equal to 5 GPa. More particularly, the range may be between 0.1 kPa and 1 MPa, or between 0.1 kPa and 100 kPa. The wide range of elastic modulus, and also the very low values of elastic modulus, reflect the instant manipulators and methods are compatible with a range of materials, able to handle extremely fragile materials that may be prone to folding, wrinkling, or other deformations or physical disruptions (e.g., tearing, fracture, etc.) during handling where there is not a uniform pressure or force over the entire material surface. Accordingly, the manipulators and methods provided herein are optionally characterized as during handling as providing movement of the manipulated material such that either no observable deformation occurs or any deformation is so minimal that there is no adverse impact on the manipulated material, such as no substantial impact on a biological function (for a biological material) or an electronic parameter (for an electronic material). In this context "no substantial impact" may refer to a measurable parameter that differs by less than 10%, less than 5% or less than 1% between pre- and post-handling by the instant manipulator.

"Thermal contact" refers to an arraignment between components such that the temperature of one component affects the temperature of a second component (e.g., heat flow) in a manner that does not adversely impact the functionality of each component.

"Thermal responsivity" refers to the amount of time it take for a material to reach within at least 95% of a steady-state temperature upon exposure to a temperature challenge. For example, a contact layer that relaxes between a thermally-actuated state and a thermally-unactuated state.

The invention can be further understood by the following non-limiting examples.

Figure 1B:
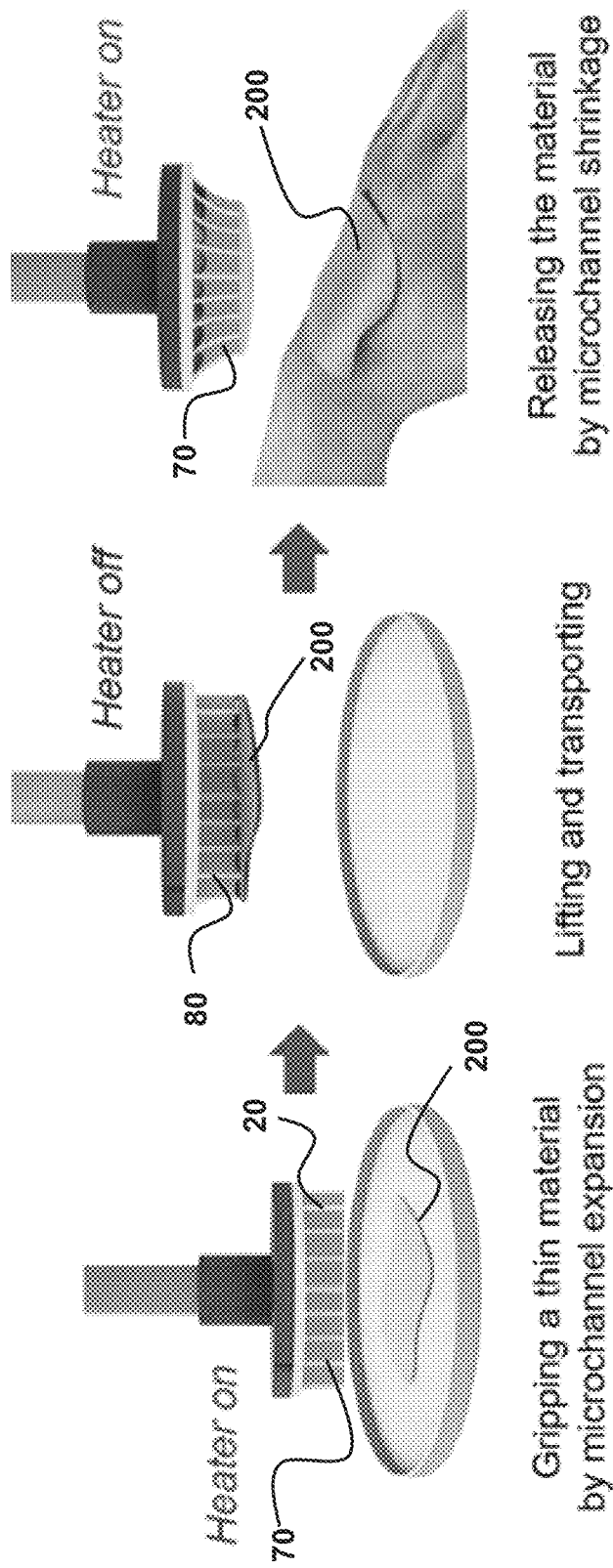

Referring to FIGS. 1A-1B, the manipulator 10 may comprise a contact layer 20 having a contact surface 30 with thermally responsive recess features 40. A microelectric heater 50 is in thermal contact with the contact surface. An electrical power source 60 is electrically connected to the microelectric heater to actuate the microelectric heater and thereby affect a controlled temperature change of the contact layer, and particularly of the thermally responsive recess features 40. In this manner, the thermally responsive recess features have a thermally actuated geometry 70 with microelectric heater actuation (FIG. 1B, left panel) and a thermally relaxed geometry 80 without microelectric heater actuation (FIG. 1B, middle panel). The thermally actuated geometry is different than the thermally relaxed geometry so that there is a pressure change within the volume defined by the recess features 40 as the volume changes for the contact surface in contact with another surface. A support substrate 300 can support and connect to the heater 50, including via an adhesive layer 100, which is particularly useful for supporting a flexible-type heater formed from a plurality of thermoresistive wires. An electrical power source 60 can be used to actuate the microelectric heater 50.

FIG. 1B illustrates transfer of a manipulated surface 200 of a transferable layer from a dish surface (left panel) to a skin surface (right panel). In this manner, there is a change in contact force between the contact layer and the contacted surface upon a change in actuation state that changes the temperature. This provides a platform for gentle and uniform change in contact force over the entire surface for manipulation, including pick-up and transfer, of a manipulated surface, including from a donor (support) substrate to a receiving substrate.

Example 1: Electrothermal Soft Manipulator Enabling Safe Transport and Handling of Thin Cell/Tissue Sheets and Bioelectronic Devices "Living" cell sheets or bioelectronic chips have great potentials to improve the quality of diagnostics and therapies. However, handling these thin and delicate materials remains a grand challenge because the external force applied for gripping and releasing can easily deform or damage the materials. This example presents a soft manipulator that can manipulate and transport cell/tissue sheets and ultrathin wearable biosensing devices seamlessly by recapitulating how a cephalopod's suction cup works. The soft manipulator comprises an ultrafast thermo-responsive, micro-channeled hydrogel layer with tissue-like softness and an electric heater layer. The electric current to the manipulator drives microchannels of the gel to shrink/expand and results in a pressure change through the microchannels. The manipulator can lift/detach an object within 10 seconds and can be used repeatedly over 50 times. This soft manipulator is highly useful for safe and reliable assembly and implantation of therapeutic cell/tissue sheets and biosensing devices.

Over the past decade, there has been great successes in assembling high performance biological and electronic materials with thin and sophisticated architecture. For example, mono-layered cell sheets have shown to reproduce physiological activities of original tissue and exhibit enhanced therapeutic efficacy than individual cells because of increased cell-cell interactions and the presence of an extracellular matrix(1-4). These cell sheets are being studied extensively to assemble in vitro disease models and treat wounded or defective tissues and organs. Separately, minimizing the thickness of wearable electronic devices enables conformal adhesion without an interfacial gap and, in turn, improves performance for sensing, diagnosis, and therapies (5-8). However, handling such delicate and thin materials for transport and assembly remains a grand challenge. External forces used for gripping, holding, and discharging such materials often deform, wrinkle, or damage materials(9). Such damage can be avoided by attaching thin materials to sacrificial polymeric supports including water-soluble or thermal release tapes (10-12). However, these supports should be removed with chemical or long-lasting heat treatment following the placement of thin materials onto a target site, thus making them not reusable.

Recently, efforts have emerged to transport thin electronic materials by simulating the ability of cephalopods (e.g., octopus, squid) to capture and release their preys(13-15). Cephalopods utilize many muscle-based suction cups, called suckers, on their arms to attain conformal adhesion to target preys in both wet and dried environments(16, 17). Bioelectrical signals control the rapid contraction and relaxation of the soft muscle and, in turn, change the internal pressure of the suckers. However, most material-handling systems that were devised to mimic the suction cups focus on recapitulating the anatomical structure but overlook the roles of the bioelectrical signal for control. Therefore, these strategies require mechanical force to be applied externally to attach and detach materials of interests. In addition, synthetic suction cups made with polydimethylsiloxane (PDMS) or polyurethane acrylates are more rigid than biological suction cups by two or three orders of magnitude(13, 15). Such rigid suction cups require higher external pressure for gripping than biological ones, thus increasing the possibility to damage thin and soft materials. Certain efforts were made to assemble a device that can hold and detach materials with heat by coating porous PDMS with thermally responsive poly(N-isopropyl acrylamide) (PNIPAAm)(14). However, the manipulation process was only possible while submerged in a water bath. In addition, it takes 30 minutes to hours for the device to move one material from one place to another.

To this end, we demonstrate a soft manipulator that can repeat the holding and unloading of thin and fragile materials within 10 seconds in response to an electrical signal. We hypothesized that a rapid thermo-responsive, microchanneled hydrogel layered with a micro electric heater would lift and release materials of interests without applying an external force due to temperature-induced internal pressure change in microchannels of the gel (FIGS. 1A-1B).

In addition, gels tailored to be as soft as biological suction cups would allow for fast and significant changes in internal pressure in response to small temperature changes while minimizing the amount of force imparted onto the thin material to be transported. We examined this hypothesis by attaching a flexible electric heater, which converts electrical signals into heat, to a micro-channeled PNIPAAm hydrogel. We examined the extent that the electrothermal signal controls the shrinkage and expansion of microchannels of the gel along with subsequent pressure change inside microchannels. The resulting soft manipulator was assessed for its ability to lift up and release thin materials onto target tissues promptly in response to the electrothermal signal. These thin materials include therapeutic stem cell sheets and ultrathin, wearable bioelectronic devices. For example, referring to FIG. 1A, the manipulator may comprise a supporter, flexible heater that can convert electrical current to heat, cyanoacrylate-based wet adhesive, and a thermo-responsive PNIPAAm hydrogel with aligned microchannels. FIG. 1B exemplifies a process to transport materials of interests using the soft manipulator. First, the soft manipulator is lowered to let the gel contact a thin material such as a therapeutic cell sheet or an ultrathin film device. During this step, the heater is turned on to contract microchannels of the gel. Second, the heater is turned off to open microchannels of the gel and generate negative pressure in microchannels. As a consequence, the gel serves to hold, lift up, and transport the thin material. Third, the heater is turned on to close microchannels of the gel and, in turn, generate positive pressure in the microchannels. The positive pressure serves to release the thin material onto the target surface.

Figure 2A:
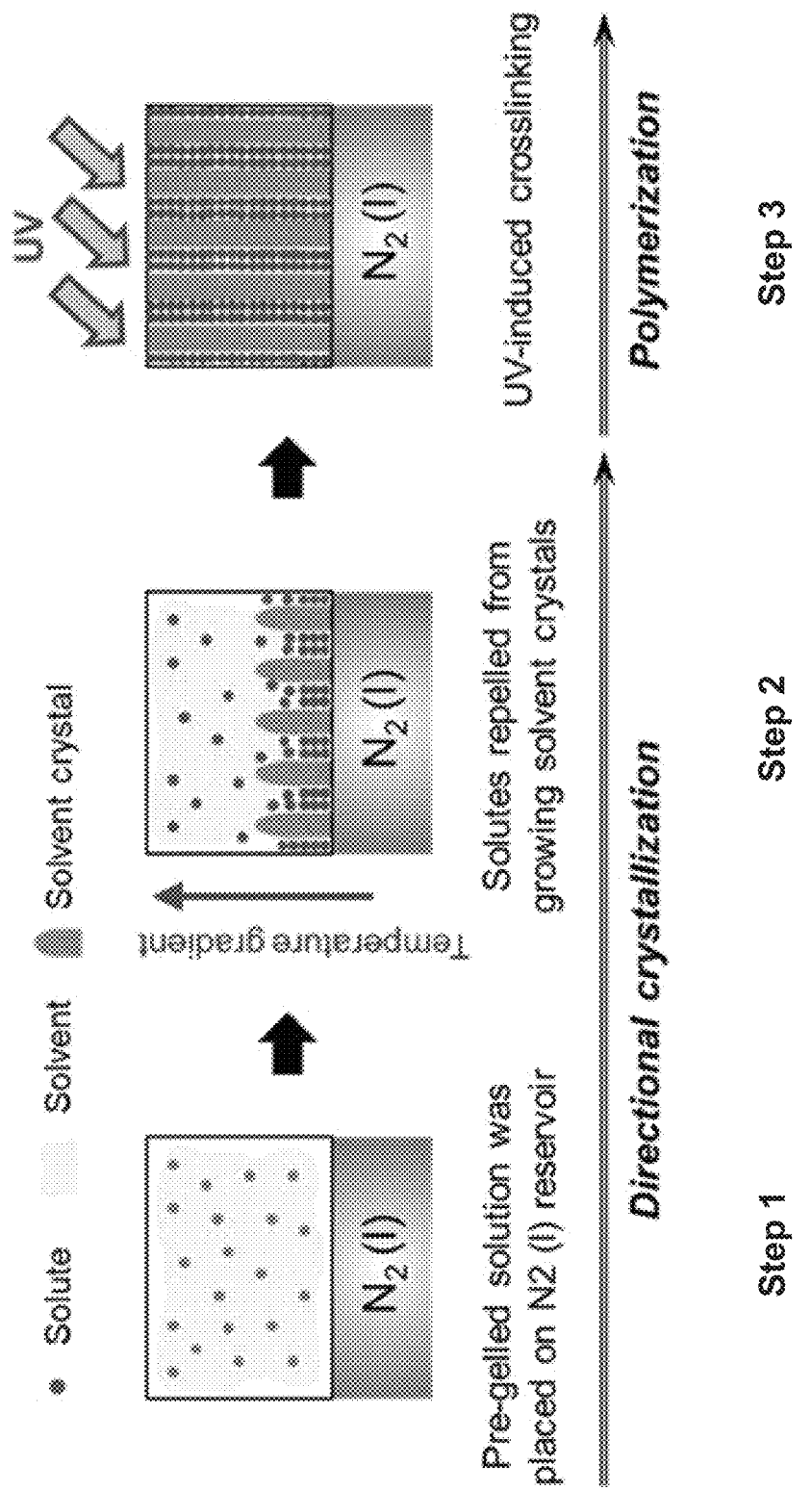
FIG. 2A-2G: Fabrication and analysis of rapid temperature-responsive gel.
Figure 2B:
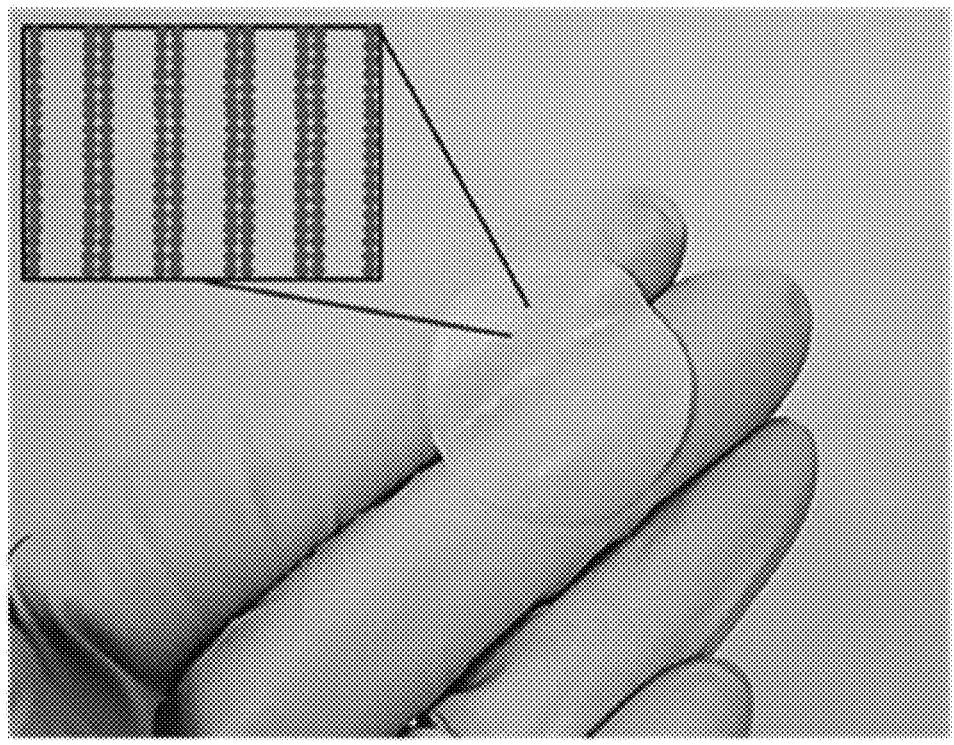
Figure 2C:
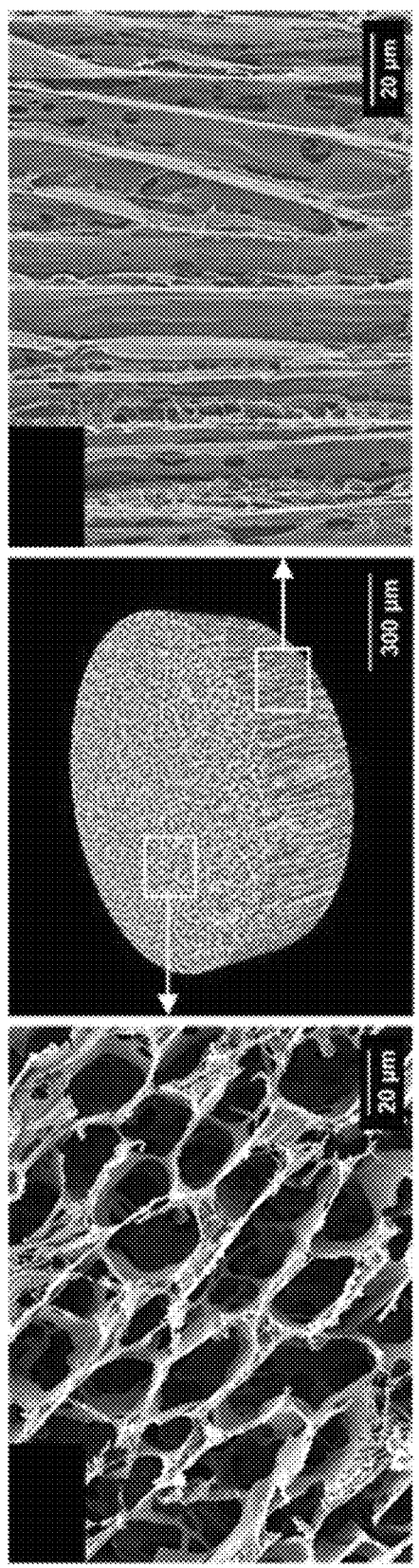

We prepared a hydrogel that undergoes a rapid volumetric change in response to a temperature change by introducing anisotropically aligned microchannels into the PNIPAAm gel. The microchanneled gel was assembled by placing the pre-gelled NIPAAm solution on top of a liquid nitrogen reservoir. Then, ice crystals nucleated from the bottom and grew to the top surface due to the temperature gradient (Step 1 in FIG. 2A). Simultaneously, solutes, including NIPAAm monomer, cross-linker, and photo-initiator in the solution were separated from the growing ice crystals because of the decreased solubility in ice crystals (Step 2 in FIG. 2A). This continuous and directional segregation of the solutes formed a cryo-concentrated phase between growing ice crystals. Subsequent exposure of the frozen sample to ultraviolet light-activated polymerization and cross-linking reaction fixed the anisotropically aligned PNIPPAm network (Step 3 in FIG. 2A)(18, 19). The final washing process with the water removed ice crystals and created a PNIPAAm gel with continuously aligned microchannels (FIG. 2B—inset). The resulting gel exhibited an average microchannel diameter of ~20±4 μm and an average wall thickness of 0.2 μm in the gel at room temperature (FIG. 2C). The porosity reached 95±1%.

For comparison, randomly oriented water crystals were created in the PNIPAAm gel by placing the pre-gelled NIPAAm solution in a freezer at −25° C. and curing it under ultraviolet light. The resulting hydrogel showed a similar porosity to the PNIPAAm gel prepared by directional crystallization. However, the microchannels of varying diameters were oriented randomly (see, e.g., FIGS. 7A-7C). In addition, PNIPAAm gel free of microchannels was prepared by skipping the crystallization step.

Figure 2D:
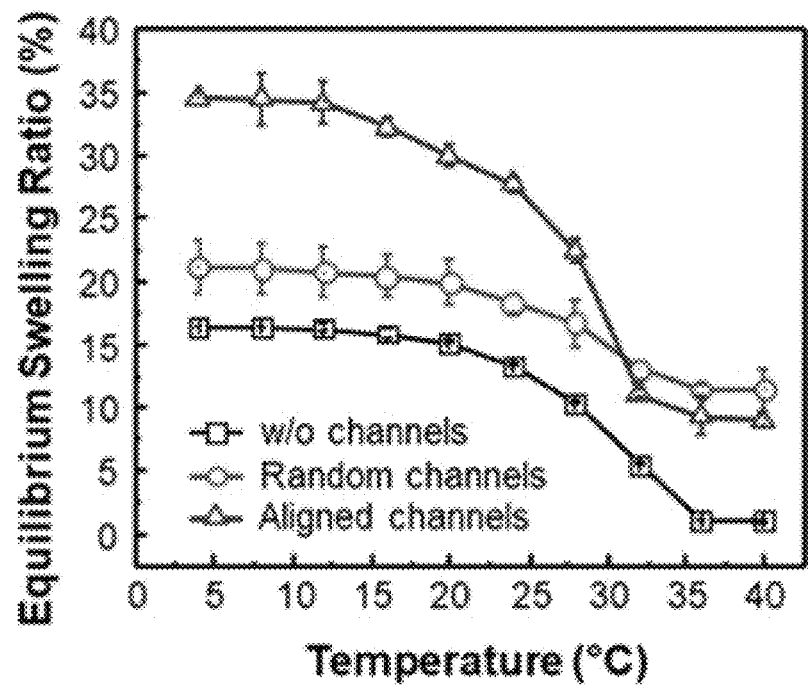
Figure 2E:
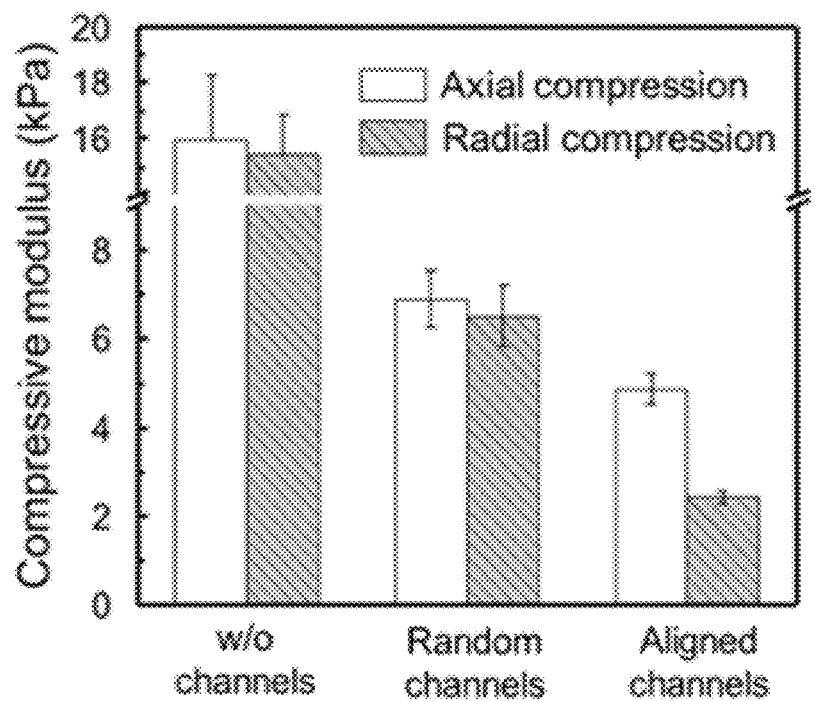

We examined the equilibrium swelling ratios of the resulting gels. All samples showed the volumetric swelling change at around 32° C., which corresponds to the lower critical solution temperature (LCST) of PNIPAAm (FIG. 2D). The difference in the equilibrium swelling ratio between 25 and 35° C. was dependent on the microchannel architecture of the gel. In particular, gels with anisotropically aligned microchannels showed a 2.7-fold higher swelling ratio than those with randomly oriented microchannels and a 1.4-fold higher swelling ratio than those free of microchannels. The elastic modulus of the gel with anisotropically aligned microchannels was dependent on the direction of microchannels (FIG. 2E). The elastic modulus measured by compressing the gel perpendicular to the microchannel was 2.4 kPa, which was 2-fold lower than that measured by compressing the gel in parallel with the microchannels. In contrast, the gel with randomly oriented microchannels and the gel free of microchannels showed the minimal dependency of the elastic modulus on the direction of compression.

Figure 2F:
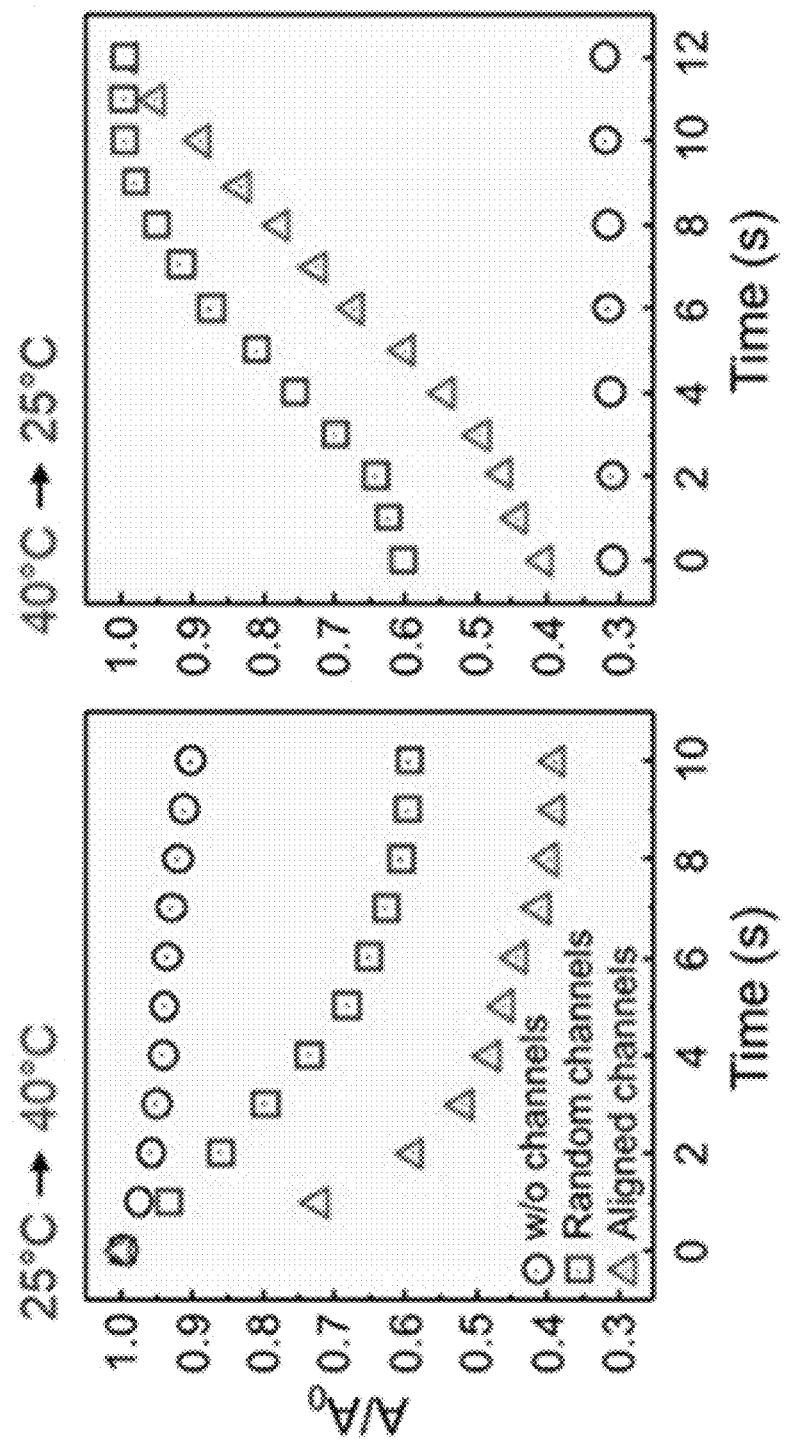

Next, we examined the extent that the microchannel architecture of the gel modulates the volumetric swelling rate in response to temperature change. The gel without microchannels exhibited minimal volumetric change over 10 seconds when the temperature was increased from 25 to 40° C. In contrast, the gel with anisotropically aligned microchannels reduced its volume by 60% within 10 seconds when temperature increased to 40° C. (FIG. 2F). This heat-triggered shrinkage is attributed to the decrease of the average cross-sectional diameter of microchannels from 20 to 9 μm as examined with scanning electron microscope images (FIG. 8A-8D). The microchannel alignment was maintained during the shrinkage. The gel with randomly oriented microchannels also shrank within 10 seconds when temperature increased to 40° C. (FIG. 2F). However, the degree of shrinkage was approximately 0.4, which was 20% lower than the gel with anisotropically aligned microchannels. The electron microscopic images showed lots of open voids as well as micropores collapsed incompletely (FIG. 9A-9D). In contrast, the gel with aligned microchannels exhibited a more uniform decrease in the microchannel diameter and minimal macro-sized voids after heating (FIG. 8A-8D). This result indicates that micropores of varying diameters and orientation limit heat-induced collapse, thus leading to the decreased volume shrinkage.

Figure 2G:
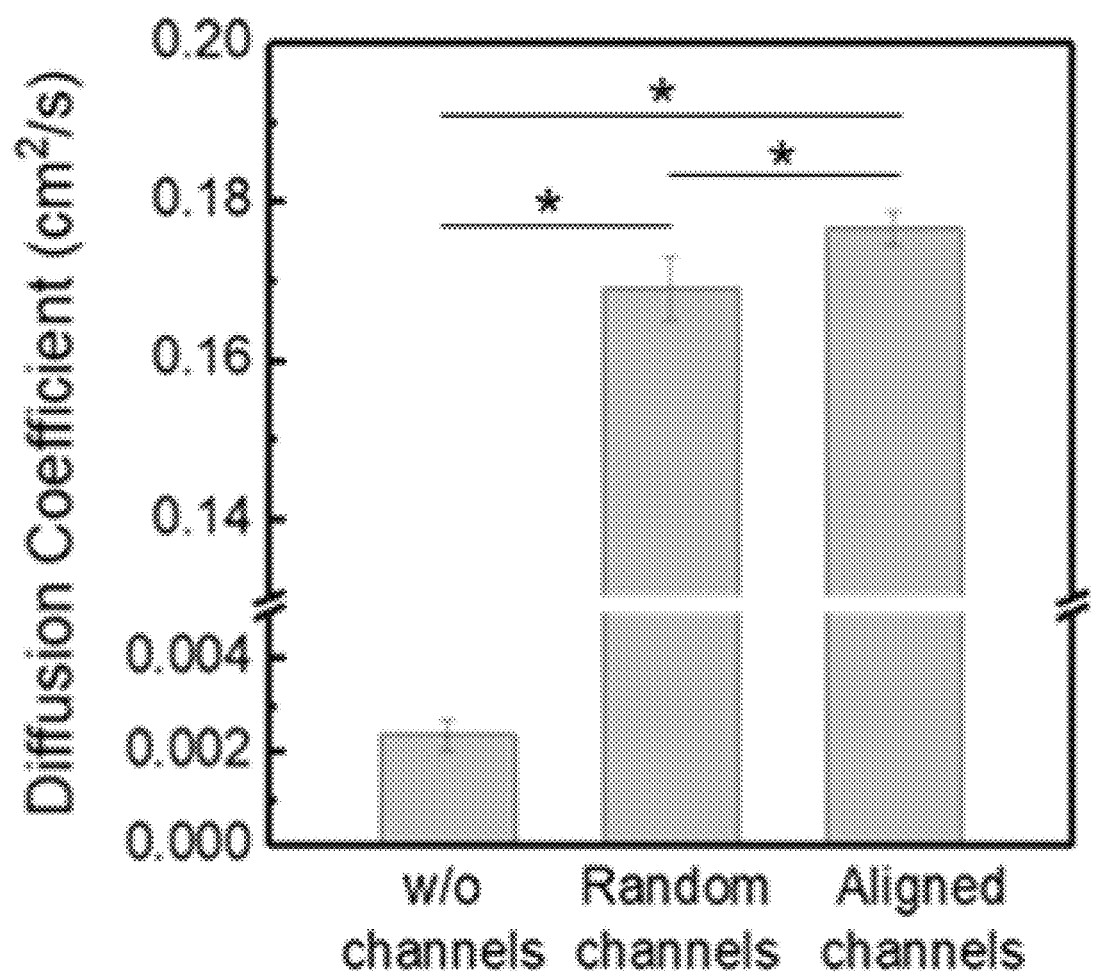

Cooling the gel from 40 to 25° C. resulted in gel expansion. The speed and degree of volumetric expansion were dependent on the microchannel architecture. The gel without microchannels did not recover its original volume even after 1 hour (FIG. 2F and FIG. 10A-10D). In contrast, both of the gels with microchannels restored their original volume within 10 seconds due to re-swelling. The reswelling plot displayed in FIG. 2F (right panel) was used to quantify the effective water diffusion coefficient (FIG. 2G). We used the Higuchi equation derived under the steady-state approximation of Fick's law of diffusion as follows(20), $$V_t = V_{25} \cdot (S/V_{40}) \cdot (D' \cdot t/\pi)^{1/2} \quad (1)$$

where $V_t$ is the volume of a gel at time t, $D'$ is an effective diffusion coefficient, S is an effective surface area. $V_{40}$ and $V_{25}$ are the volume of a gel at 40° C. and 25° C., respectively. We assumed that water diffusion occurred exclusively on the gel surface. Anisotropically microchanneled gels had a 75-fold higher water diffusion rate than the gel free of microchannels (FIG. 2G). Also, the gel with anisotropically aligned microchannels showed a 10% higher water diffusion rate than that of the gel with randomly oriented microchannels.

Figure 3A:
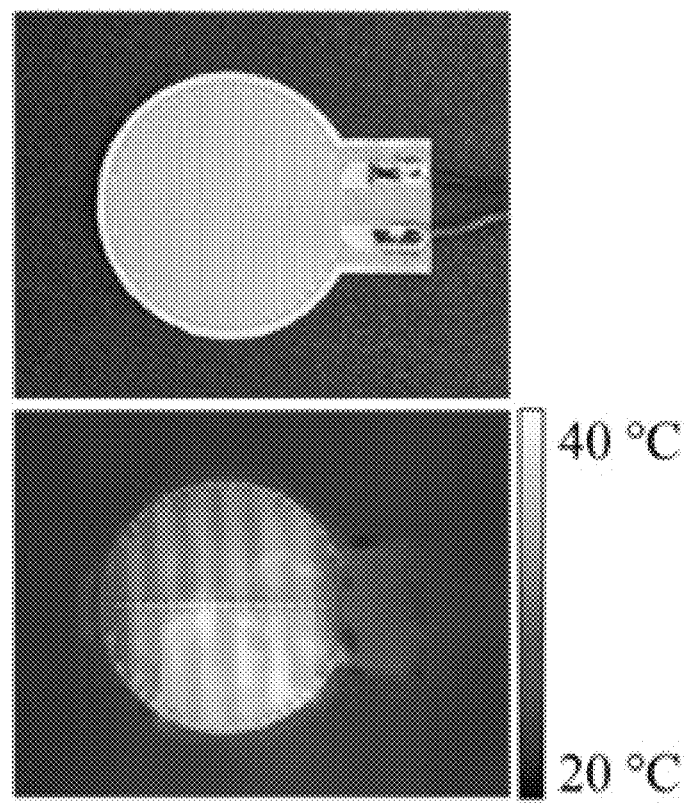
FIG. 3A-3E: Design of soft, electrothermal soft manipulator.
Figure 3B:
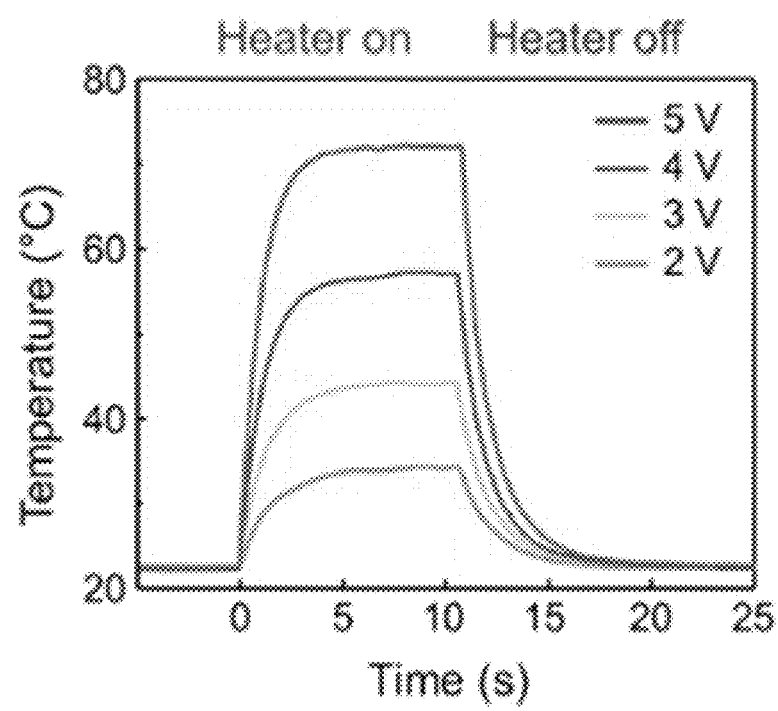
Figure 3C:
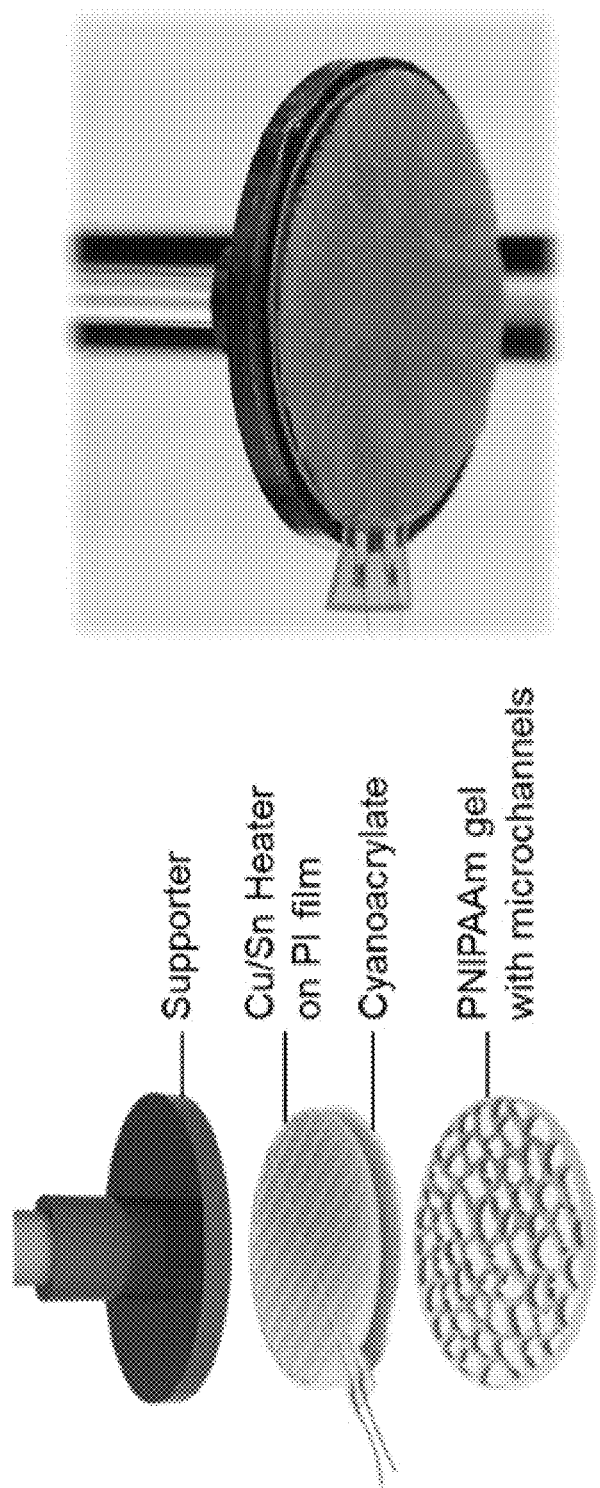

Separately, a flexible electric (Joule) heater was fabricated to be attached to the gel by photolithographic patterning of a copper/polyimide film (thickness: 9 μm copper/12 μm polyimide). The line width and spacing of the copper pattern was kept at 300 μm to provide uniform heat across the gel disk (FIG. 3A). The heater was additionally coated with a layer of tin (thickness: ~1 μm) to prevent oxidation of the copper at an increased temperature within a humid environment. The heater was then connected to an external power supply with a voltage range of 2-5 V (FIG. 3B). The activated temperature was examined using an infrared camera, showing that the heater reached the target temperature at 37° C. within 5 seconds after applying a voltage of 2 V (FIGS. 3A and 3B). After the power was turned off, the temperature was dropped immediately back to 25° C. Such electrothermal heater was attached to the gel disk using a cyanoacrylate-based adhesive(21). The bi-layered hydrogel-heater construct was finally attached to a 3D printed supporter (FIG. 3C).

Figure 3D:
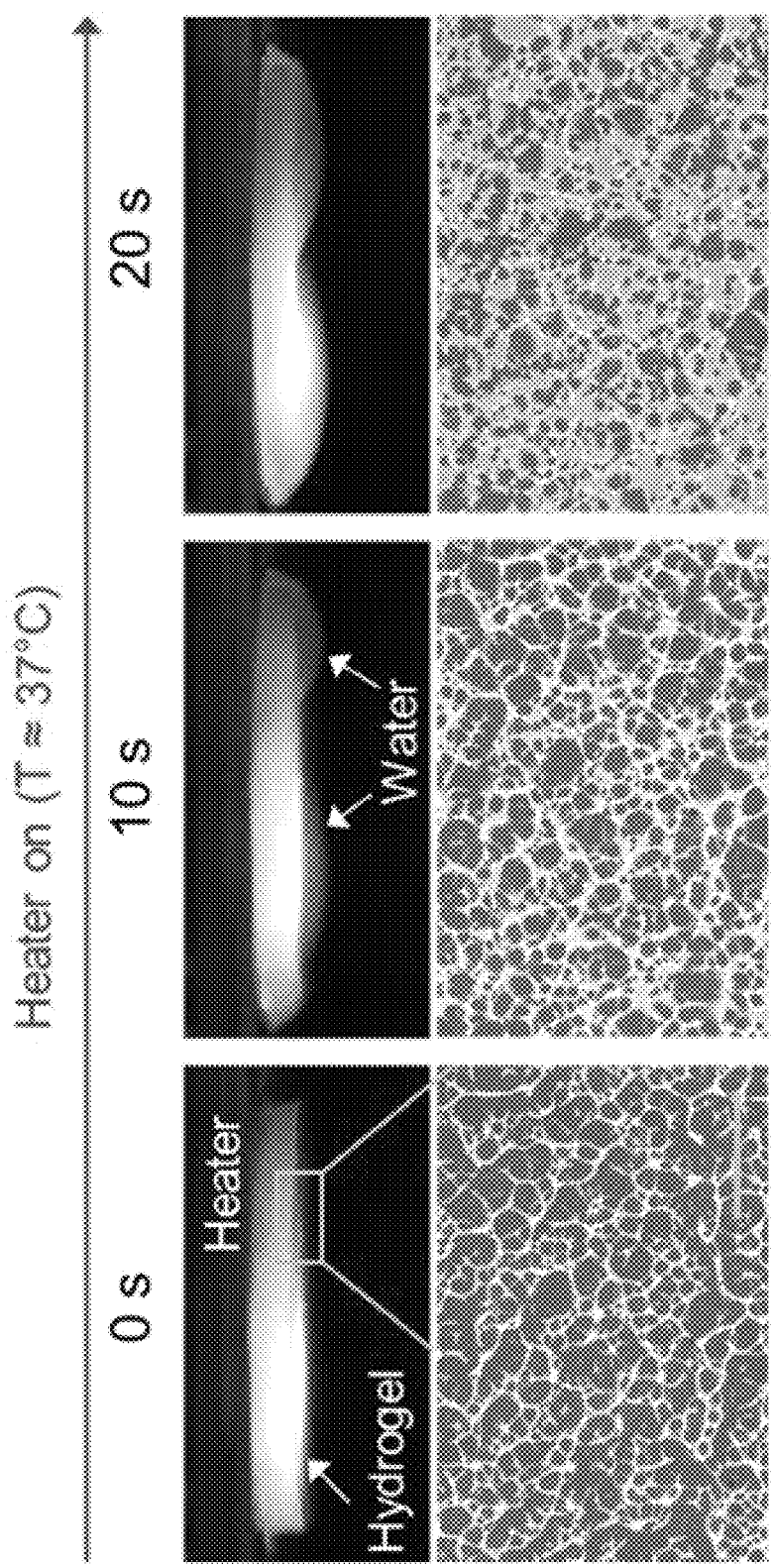
Figure 3E:
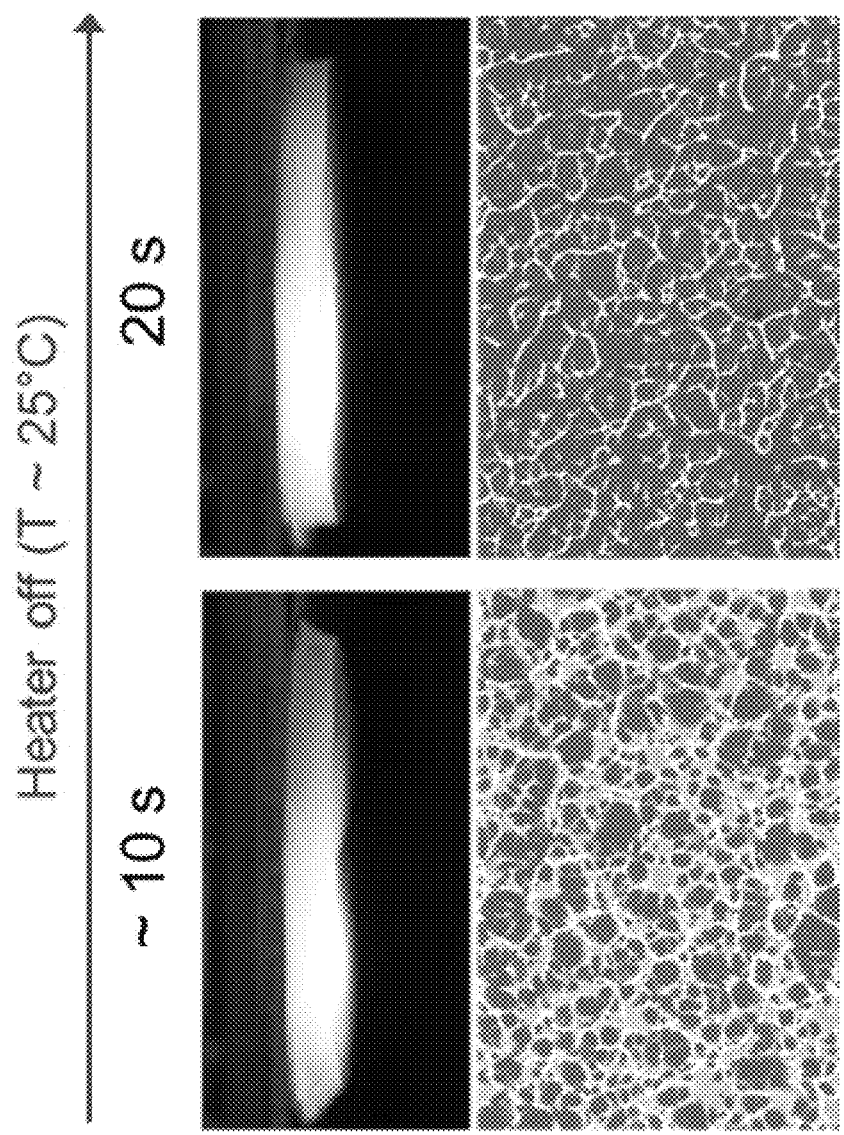
Figure 11A:
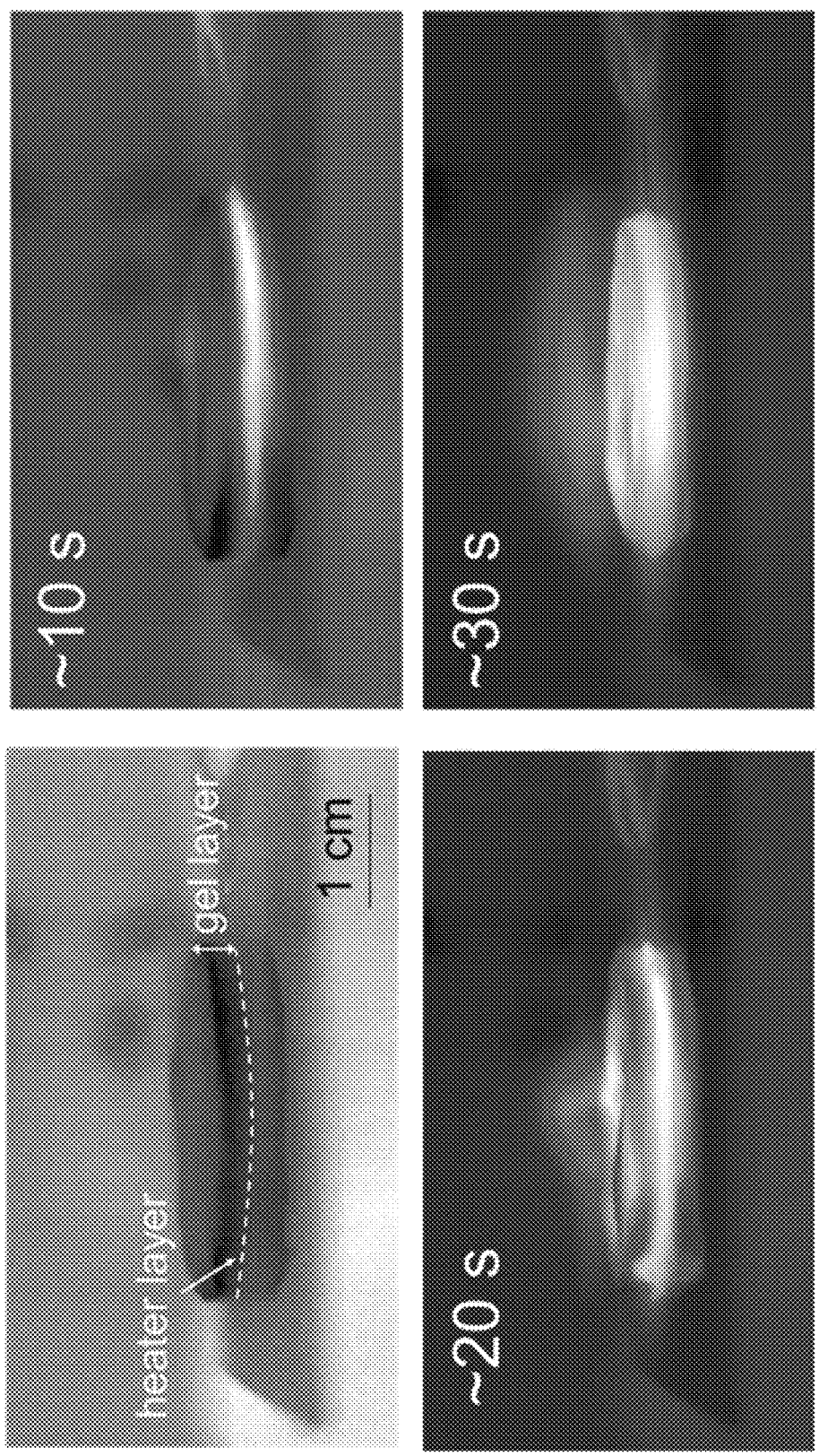
FIGS. 11A-11C: Heat transfer properties of the soft manipulator.
Figure 11B:
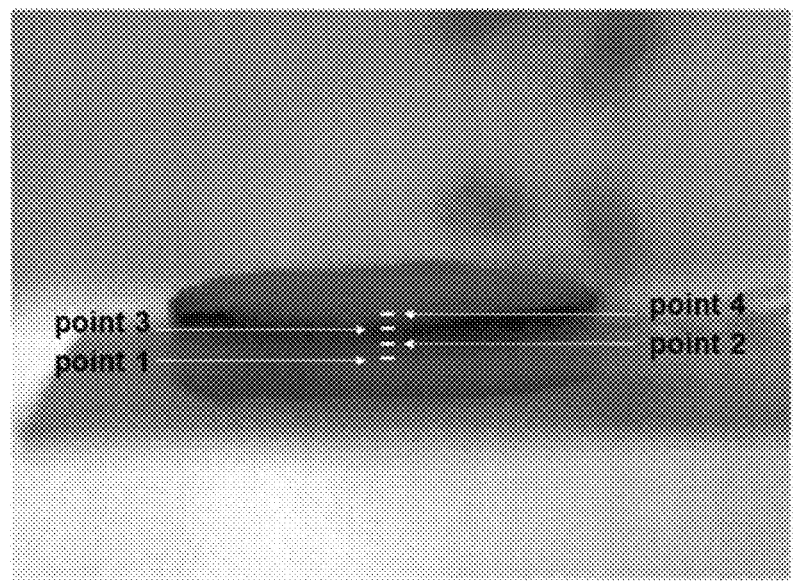
Figure 11C:
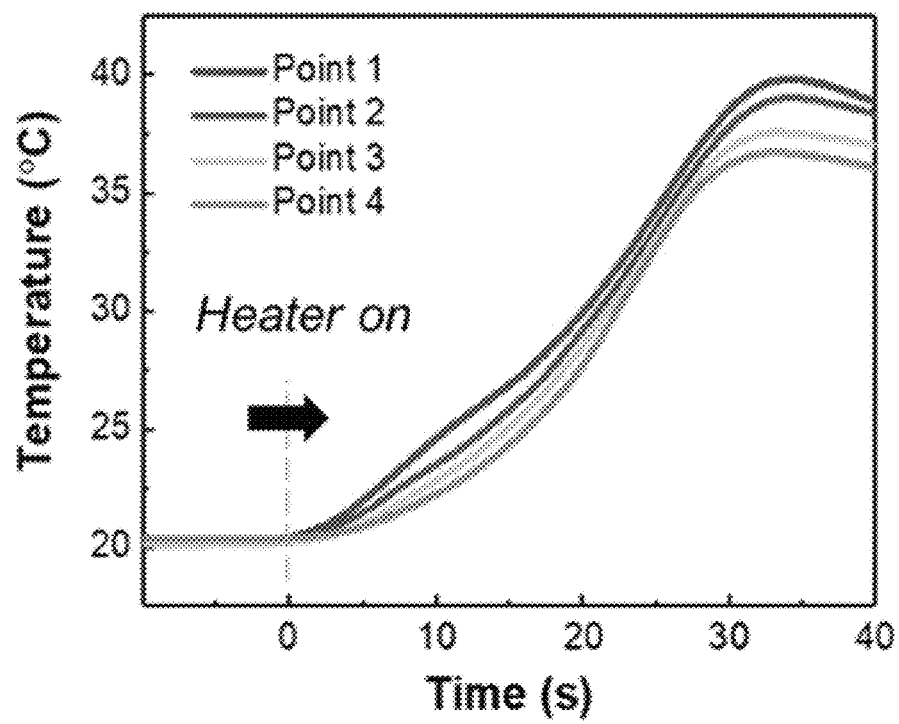

With the resulting electrothermal soft manipulator, we examined the response of the gel disk to the electrical signal. The test was conducted outside water. FIGS. 3D and 3E show the side-view of the gel disk and the microstructural changes of the gel surface during the electrically controlled heating and cooling cycle. Switching on the heater triggered shrinkage of microchannels within 10 to 20 seconds and simultaneously released a fraction of water from the gel (FIG. 3D). With the power off, the gel expanded the microchannels and reabsorbed the water within a few seconds (FIG. 3E). The shrinkage and expansion of microchannels could be repeated hundreds of times by turning the power on and off. No structural failure of the gel was observed during repeated operation. We further examined the heat transfer through the gel layer placed on the heater at a temperature of 40° C. (FIG. 11A). With the heater on, the temperature of the gel increased rapidly from the bottom (point 1 in FIG. 11B) to a top (point 4 in FIG. 11B) within 20 seconds. This result confirms heat propagation along the gel thickness direction. The gel temperature increased at a rate of 0.3° C./mm·s, independent of the region of observation. Finally, the temperature of the entire gel became equal to that of the heater within 30 seconds (FIG. 11C).

Figure 12:
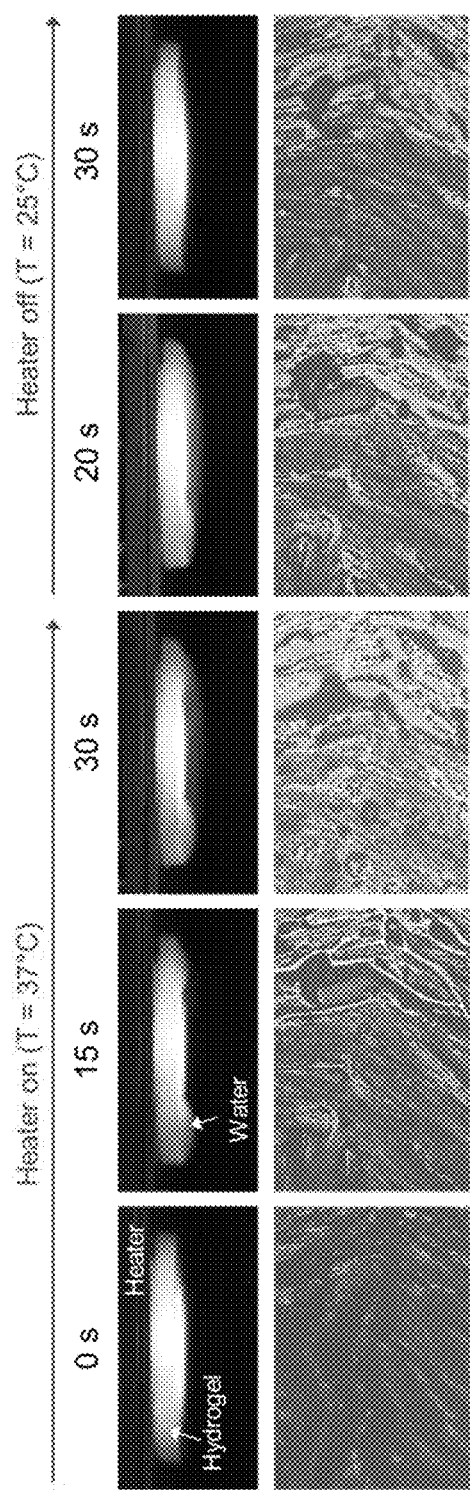
FIG. 12: Snapshots of the gel with randomly oriented microchannels when the heater was turned on and off (upper images). Below images are optical microscopic images of the corresponding surface of the gel. The dark area represents the gel bulk, and the bright area represents the wall of microchannels.
Figure 13A:
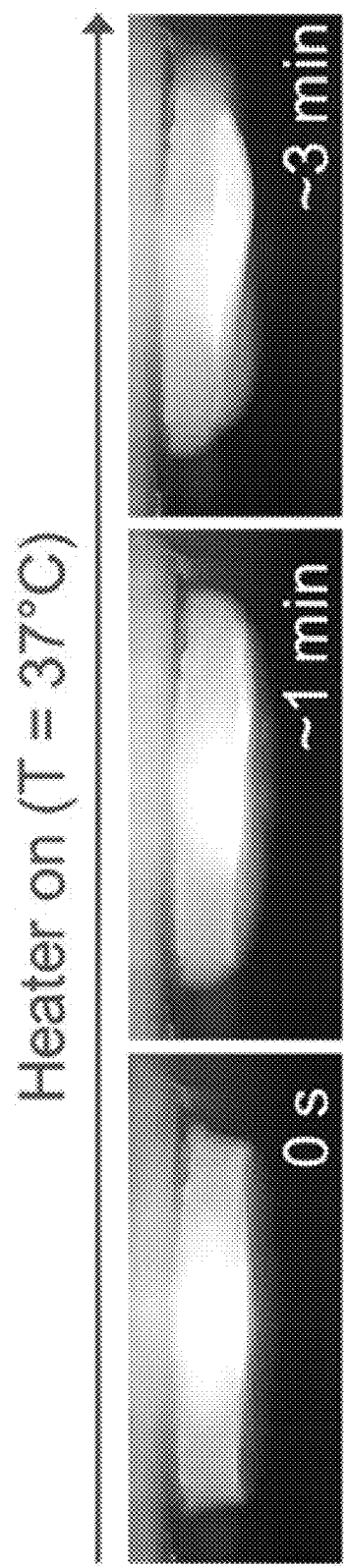
FIGS. 13A-13B: Snapshots of the gel without microchannels when the heater was turned on (FIG. 13A) and turned off (FIG. 13B).
Figure 13B:
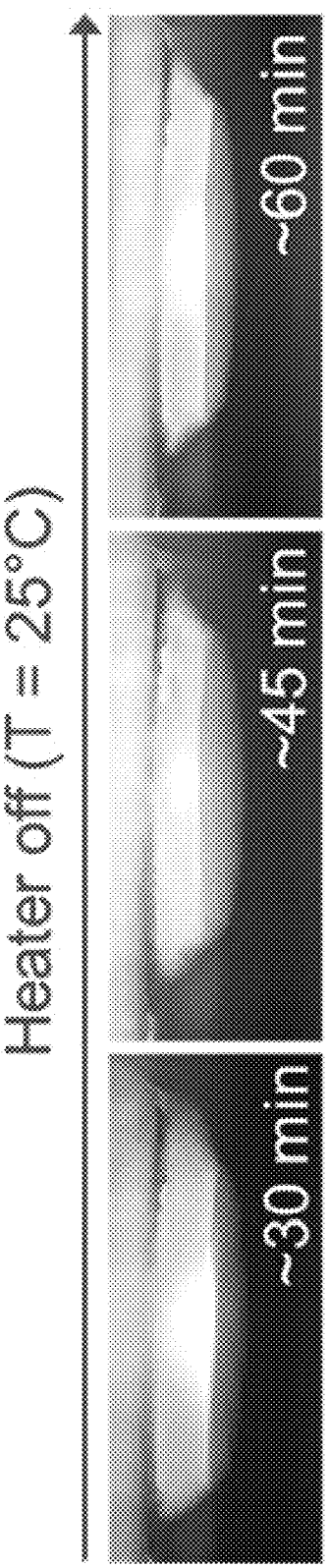

The gel with randomly oriented microchannels also underwent shrinkage and expansion in response to the electrothermal signal. However, the area undergoing microchannel shrinkage and expansion was not as uniform as in the gel with anisotropically aligned microchannels (FIG. 12). Therefore, the gel released water locally. The gel without microchannels showed a very slow release and limited absorption of water when the electric heater was on and off, respectively (FIG. 13A-13B).

Figure 4A:
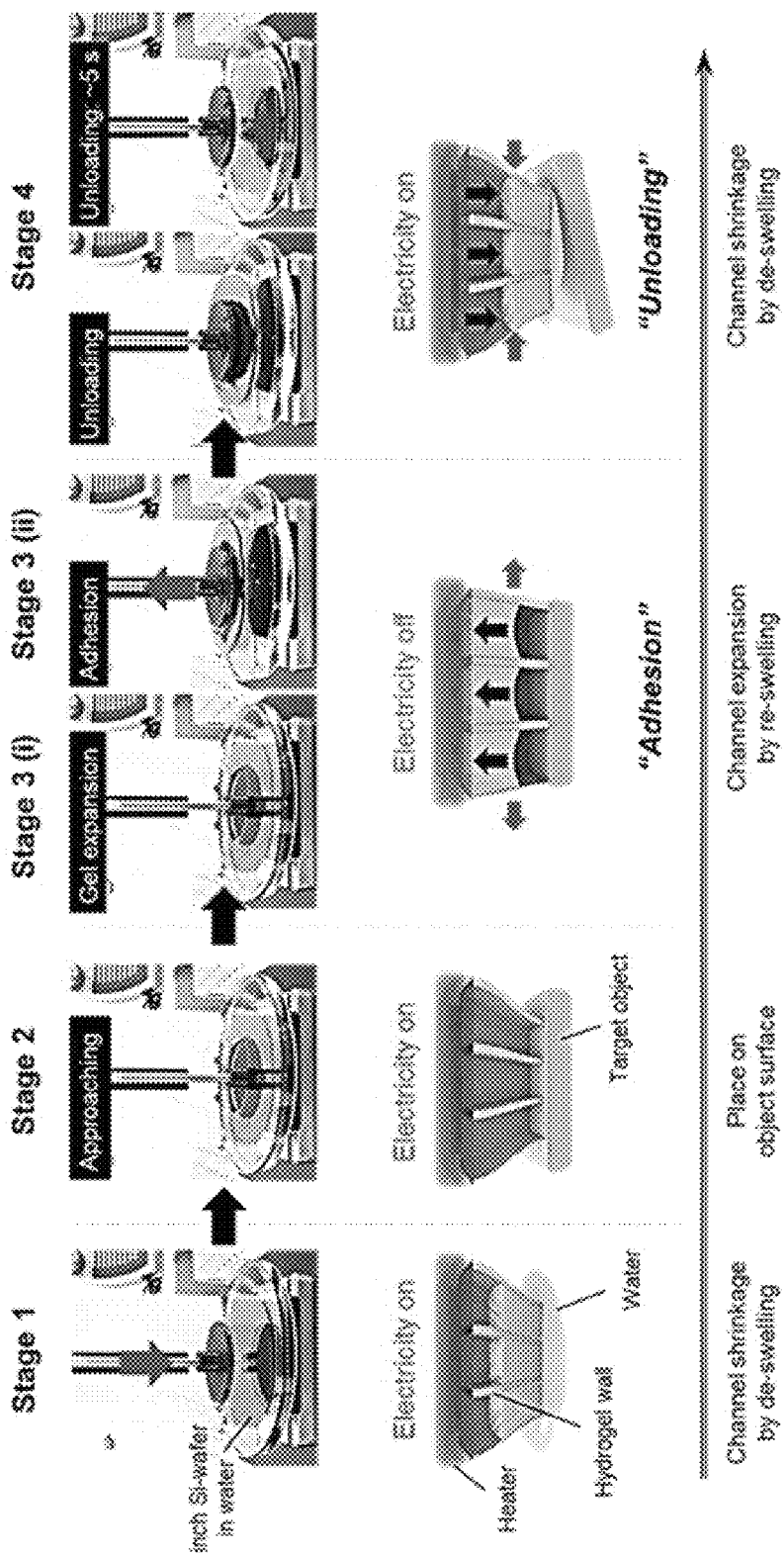
FIG. 4A-4F: Working mechanism and characterization of the soft manipulator.
Figure 4B:
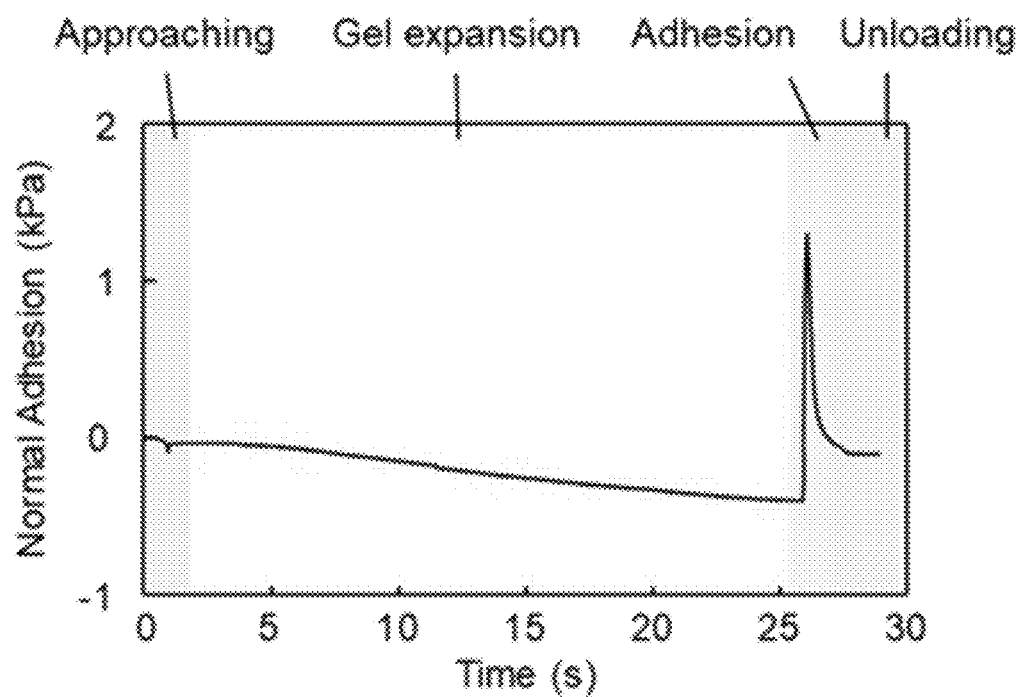

The shrinkage and expansion of anisotropically aligned microchannels allowed the gel (contact layer) to grip, lift, and release materials of interest (FIG. 4B). The manipulator with a diameter of 25 mm was used in this study. The manipulation process was conducted as follows: First, we shrank the upper part of the microchannels of the hydrogel by activating the heater (Stage 1 in FIG. 4A). During this process, the gel released a fraction of water, thus creating an empty pocket between the heater and residual water in the microchannels. The gel was then placed on a 4-in diameter silicon wafer, a model material that should be transported (Stage 2 in FIG. 4A). Next, the heater was deactivated to expand the shrunken microchannels and move residual water upward (Stage 3($i$) in FIG. 4A). The subsequently formed vacant space between water within the microchannels and the silicon wafer decreased the pressure inside microchannels, thus making the gel adhere to the silicon substrate. Thus, the soft manipulator could lift the substrate (Stage 3 ($ii$) in FIG. 4A). Finally, with the power on, microchannels adjacent to the heater shrank and pushed water out of the microchannel (Stage 4 of FIG. 4A). The subsequent pressure increases inside the microchannels served to dislodge the silicon wafer quickly. This mechanism is distinct from artificial handling systems assembled with an inspiration from anatomy of the Cephalopods suction cup. These handling systems, however, require external force to hold and release materials of interest. In contrast, the manipulation process performed by our soft manipulator resembles the neuromuscular actuation in which Cephalopods grip and release materials of interest. Through control of electricity, the rapid electrothermal actuation of the gel enabled the manipulator to systematically lift up and release target materials without external forces, but rather is accomplished via a change in temperature.

The normal pressure development of the gel to the silicon surface was further measured, particularly during Stage 2 and 3. This measurement was conducted by attaching the bi-layered gel-heater construct to a dynamic mechanical analyzer (DMA) (FIG. 4B). First, the gel was pre-heated by the heater and brought into contact with a 4-inch silicon wafer ("Approaching" stage in FIG. 4B). Next, when the power was turned off to expand microchannels, the load was increased in the negative direction for 25 seconds ("Gel expansion" stage in FIG. 4B). This bi-layered gel-heater construct was then slowly pulled upward at 0.1 mm/s by DMA to monitor the increase of the adhesion strength ("Adhesion" stage in FIG. 4B). The maximum adhesion strength reached 1.5 kPa. Once the power was turned on before the stress reached 1.5 kPa, the normal adhesion strength decreased quickly to 0 kPa within 5 seconds ("Unloading" stage in FIG. 4B).

Figure 14A:
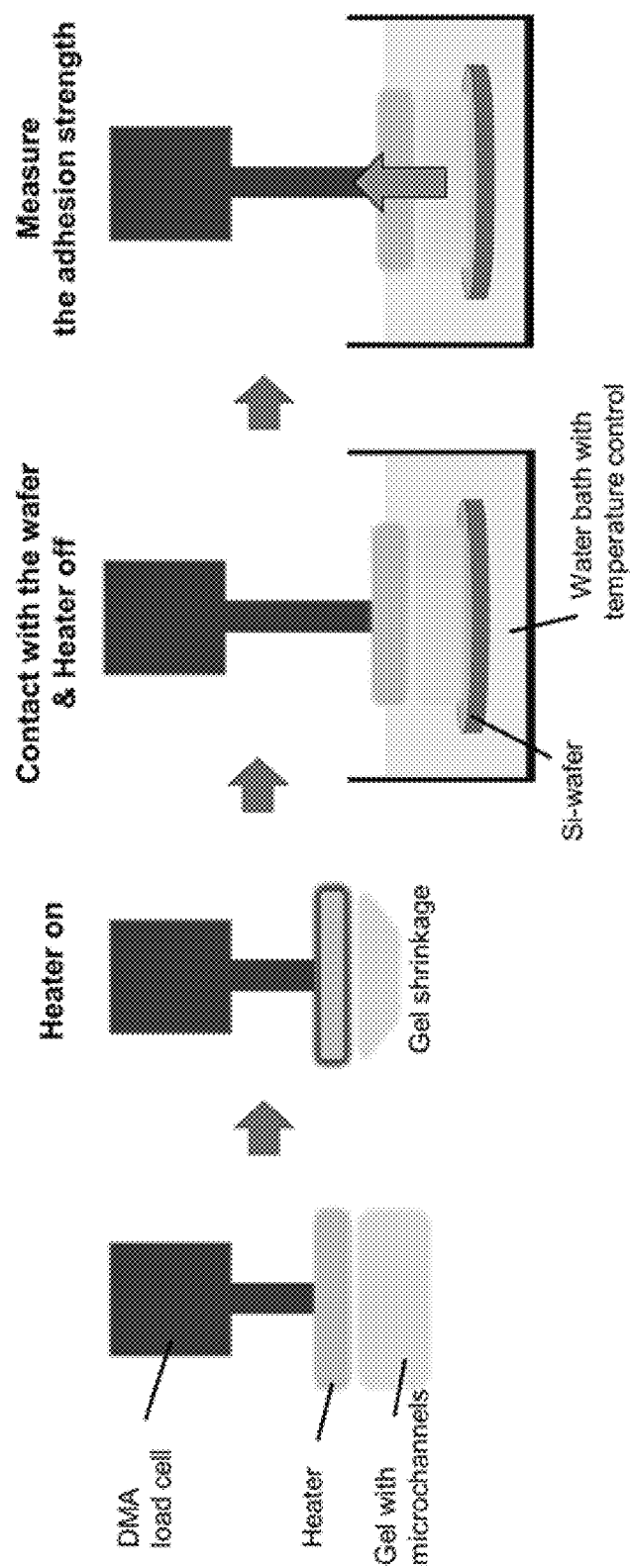
FIGS. 14A-14B: The adhesion strength under controlled temperatures.
Figure 14B:
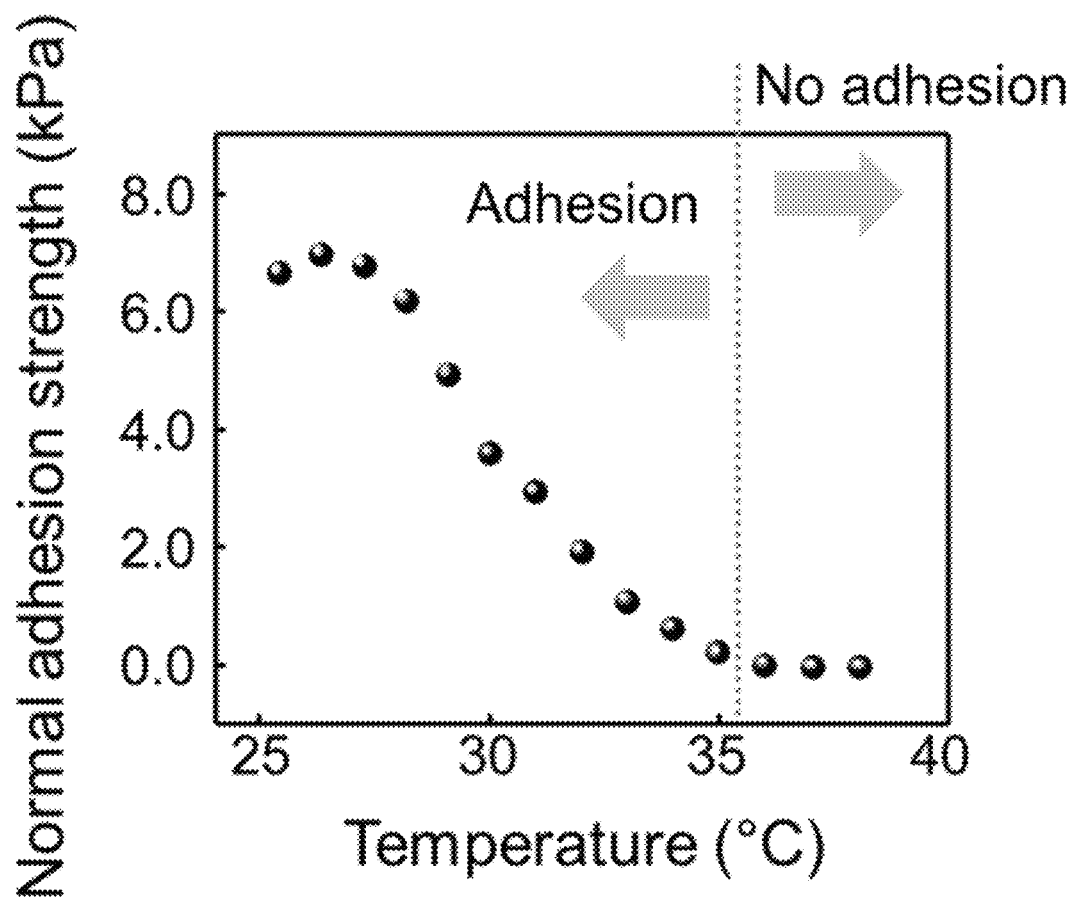

Interestingly, without temperature control, the manipulator does not exhibit adhesion. We further examined whether temperature-induced contraction and expansion of microchannels are essential to create adhesion. The soft manipulator pre-heated to 37° C. was placed on the silicon wafer immersed in water with controlled temperatures. Then, the heater of the soft manipulator was turned off. Interestingly, at temperatures below LCST of the gel layer (i.e., ~32° C.), the adhesion strength increased rapidly with decreasing temperatures (FIG. 14A-14B). This result confirms that temperature of the heating layer in the manipulator controls the degree of expansion of the micro-channeled gel layer and, in turn, regulates adhesion strength.

Figure 4C:
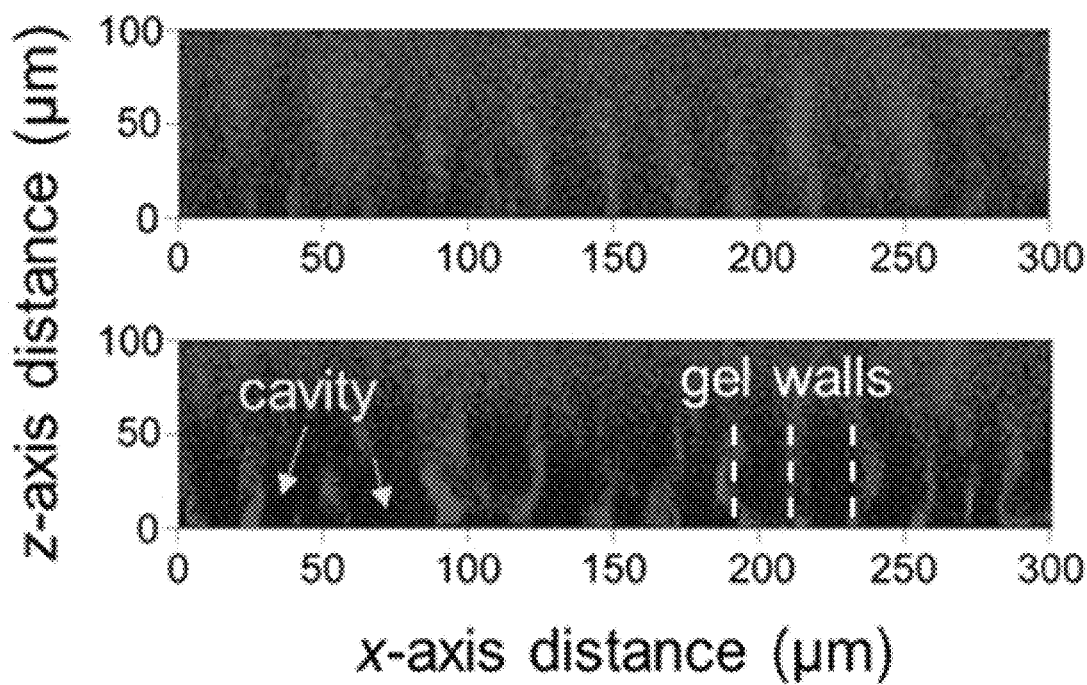
Figure 4D:
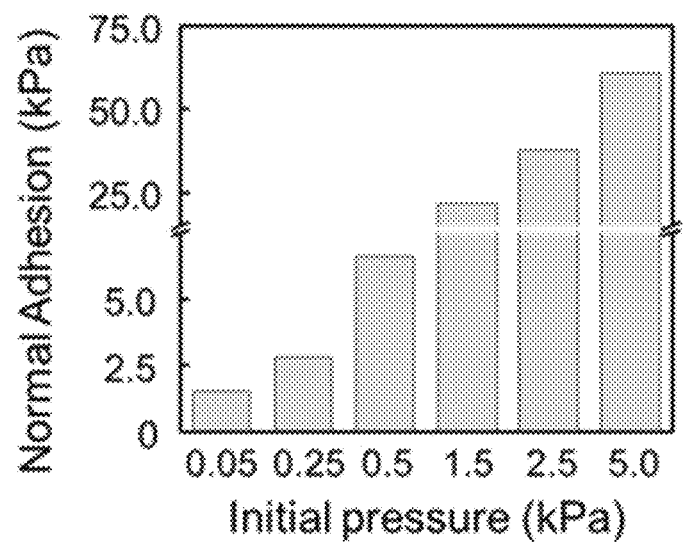

We propose that the electrothermally controlled adhesion of the gel to the silicon wafer results from the pressure difference (ΔP) between two ends of microchannels. We introduced the mixture of rhodamine B and water into microchannels of the gel and monitored the vertical movement of water through the individual microchannel during Stage 3($i$) in FIG. 4A. According to the side view of the gel captured with confocal microscopy, the microchanneled gel disk was fully filled with water (upper image in FIG. 4C). Heating and the subsequent cooling process resulted in the space in the lower part of the microchannel adjacent to the silicon substrate by moving residual water upward in the microchannels (lower image in FIG. 4C). This image is similar to the scheme that represents Stage 3 in FIG. 4A. The average height of space in the microchannel was approximately 50 µm. The pressure difference of a single microchannel in the gel was quantified with a height of the empty part in the microchannel as follows:

$$\Delta P = \rho_w \cdot g \cdot (h_i - h_f) \qquad (2)$$

where $\rho_w$ is the density of water, g is gravitational acceleration, $h_i$ and $h_f$ are the height of the space in microchannels when the power was turned on and off, respectively. According to the calculation, each microchannel in the gel produced 0.5 Pa of negative pressure after the cooling process.

Figure 15A:
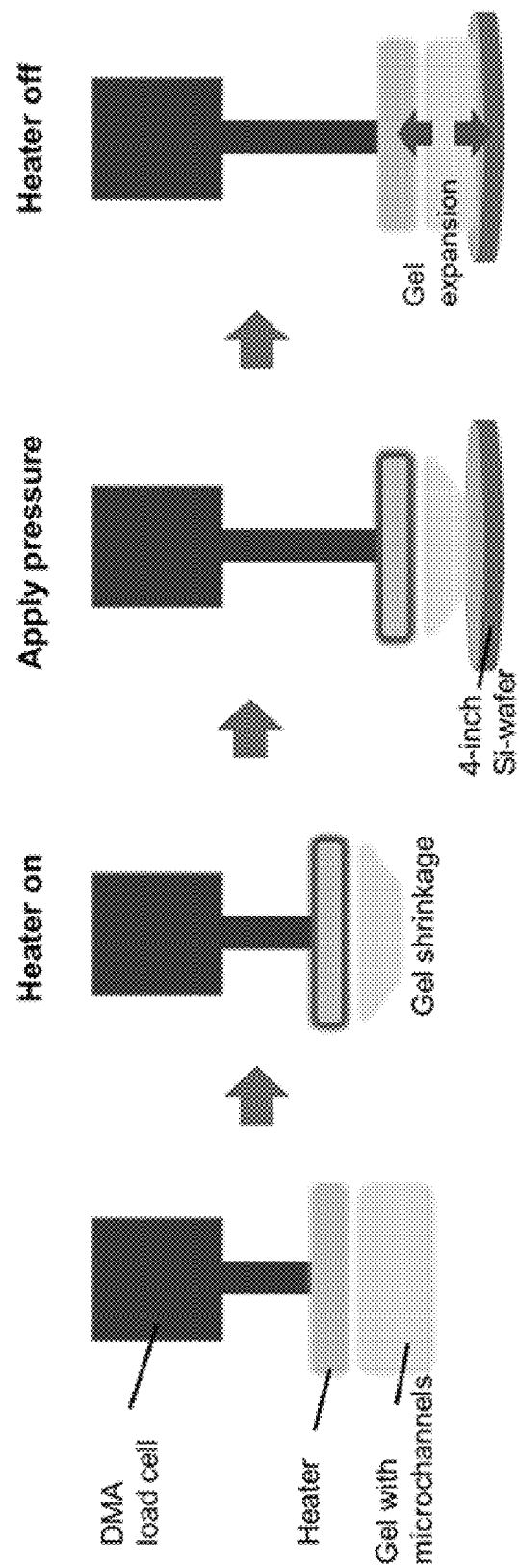
FIGS. 15A-15B: The normal pressure development under different initial contact pressures.
Figure 15B:
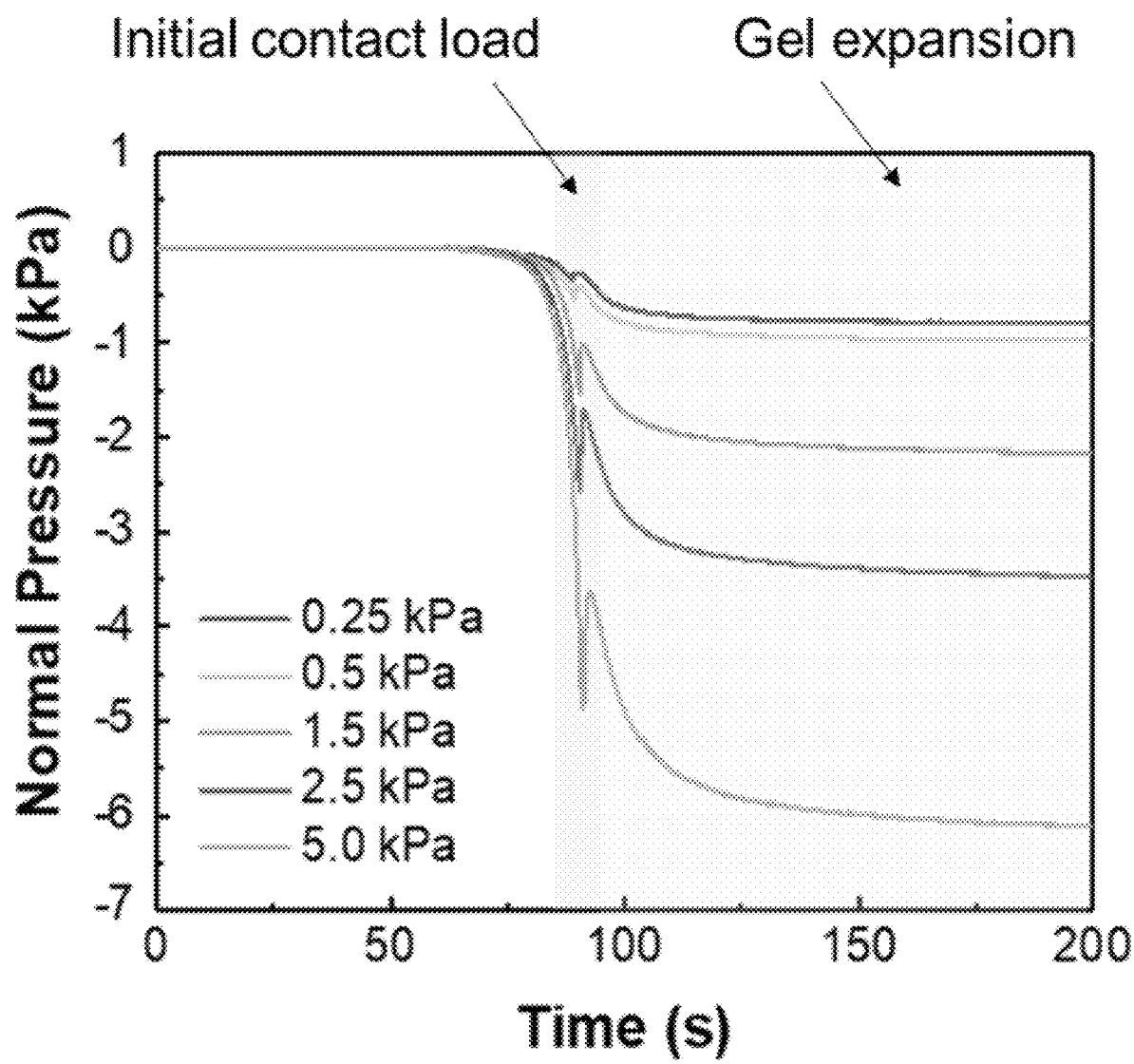

Interestingly, the adhesion strength of the gel to the silicon wafer was dependent on the initial load applied to the soft manipulator (FIG. 3D). The maximum adhesion strength reached 65 kPa with the initial pressure of 5.0 kPa. To underlie the mechanism, we examined the normal pressure development that varies with the initial contact pressure using a DMA. As shown in FIG. 15A, the heated soft manipulator was placed on the target silicon wafer. As soon as the heater was turned off, the gel layer expanded and pushed the silicon wafer more strongly. As a consequence, the normal pressure developed in the opposite direction. The normal pressure increased with the initial contact pressure (FIG. 15B). Increasing the initial contact pressure enlarged the effective suction area of the soft manipulator and also augmented the normal pressure.

Figure 4E:
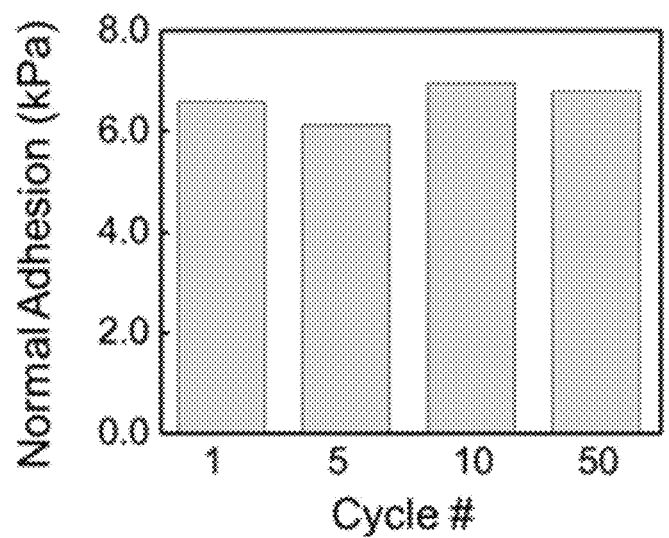
Figure 4F:
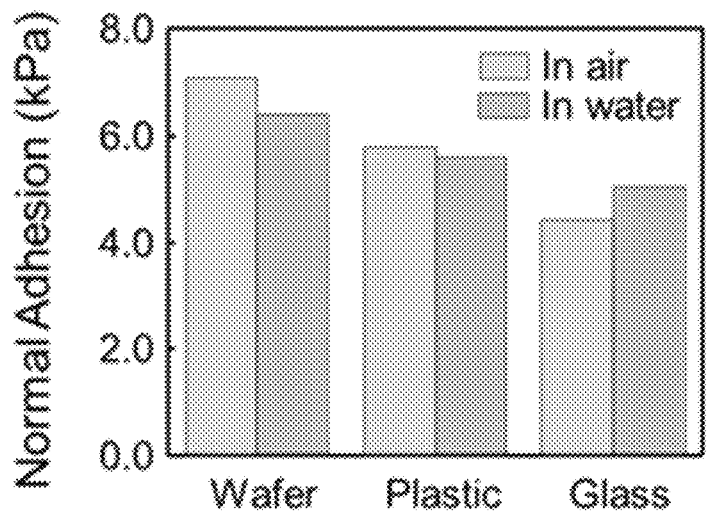
Figure 16A:
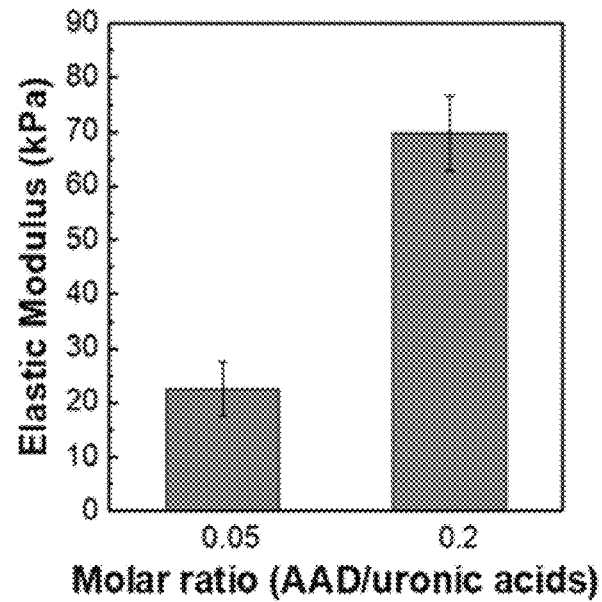
FIGS. 16A-16B: The normal pressure development against different target materials.
Figure 16B:
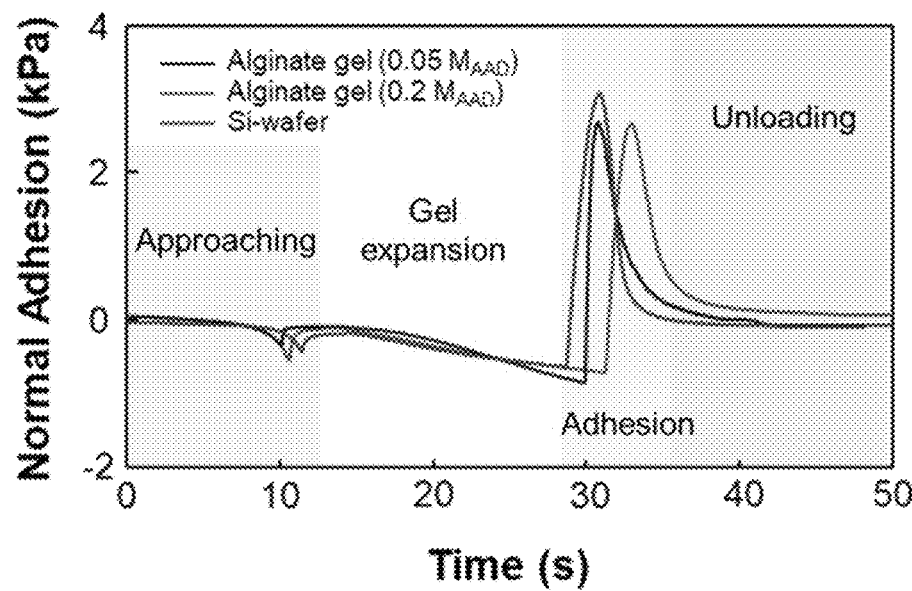
Figure 17:
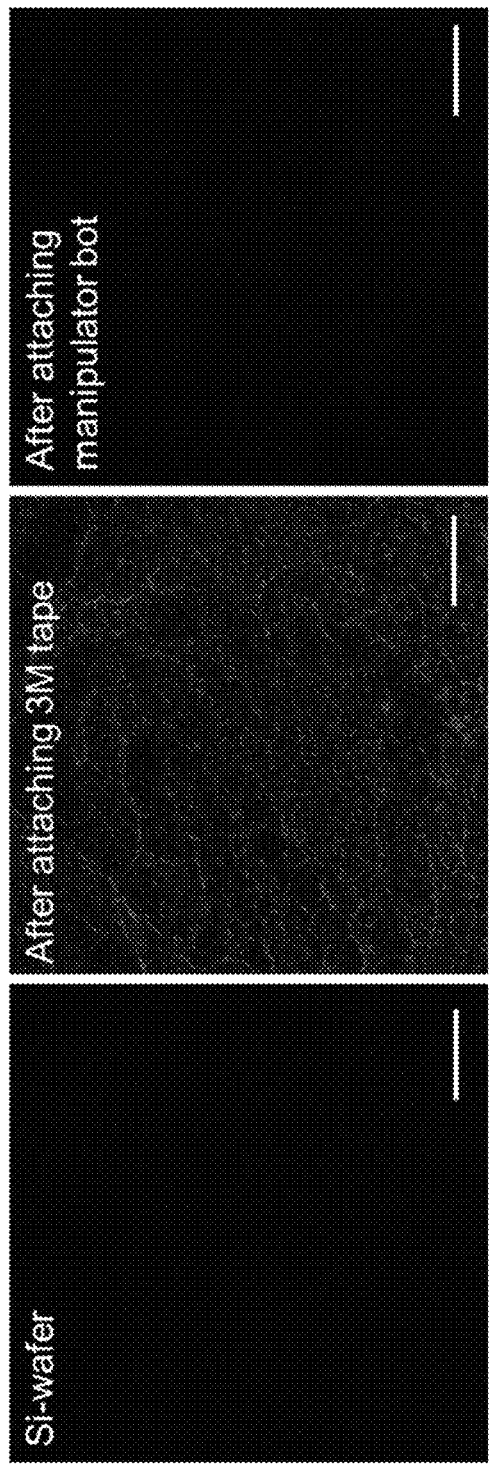
FIG. 17: Fluorescence images of the surface of silicon wafers before and after the adhering process. Samples were incubated with Rhodamine B for 30 minutes after performing the adhesion test.

We also examined the effect of elastic modulus of target materials on the adhesion strength. We prepared alginate hydrogels with elastic moduli of 22.5 and 69.8 kPa as target materials for transport (FIG. 16A). As confirmed with the pressure development profiles, with a given initial contact pressure of 0.25 kPa, the soft manipulator exhibited a similar magnitude of the adhesion strength to the alginate gels as well as the silicon wafer with a much higher elastic modulus of 140-180 GPa. This result suggests that it is not necessary to vary the initial contact pressure with the target material stiffness (FIG. 16B). The adhesion strength was not reduced during the repeated cycles of closure and opening of microchannels (FIG. 4E). No chemical contamination or residue was observed on the silicon wafer after the process (FIG. 17). The soft manipulator could transport plastic and glass materials by exerting a similar magnitude of the adhesion strength regardless of material hydrophobicity (FIG. 4F). More interestingly, the soft manipulator functioned to transport materials immersed in aqueous media and those in the air. Accordingly, the manipulators and related handling methods are compatible with transfer of materials immersed in a gas (e.g., air) or liquid.

Figure 5A:
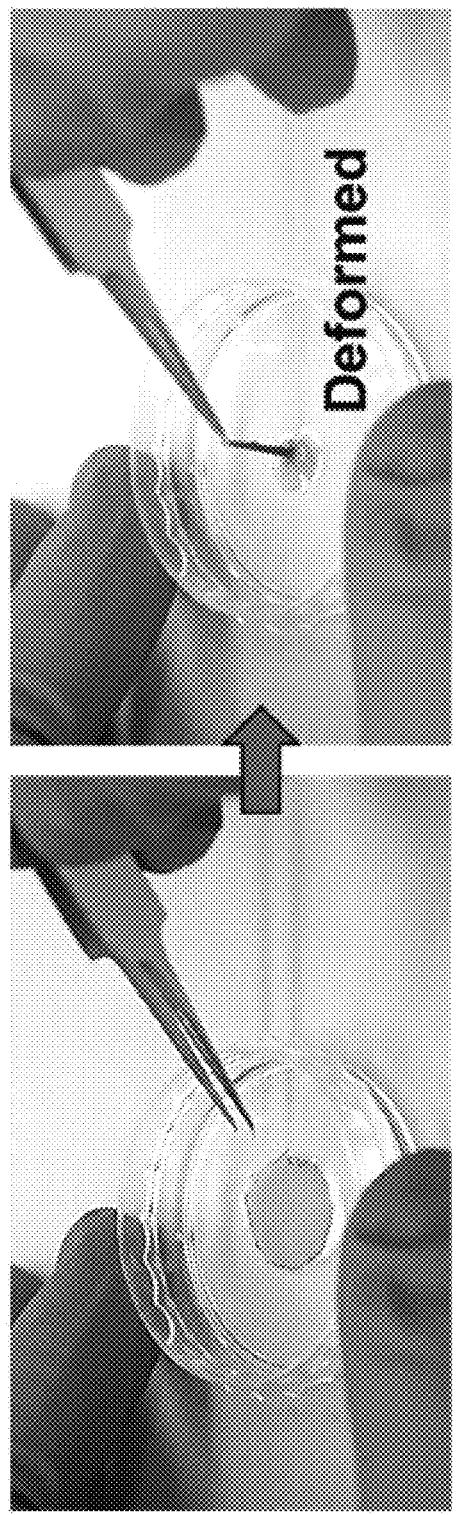
FIG. 5A-5G: Demonstration of the ability of the soft manipulator to transport cell sheets to target sites.
Figure 5B:
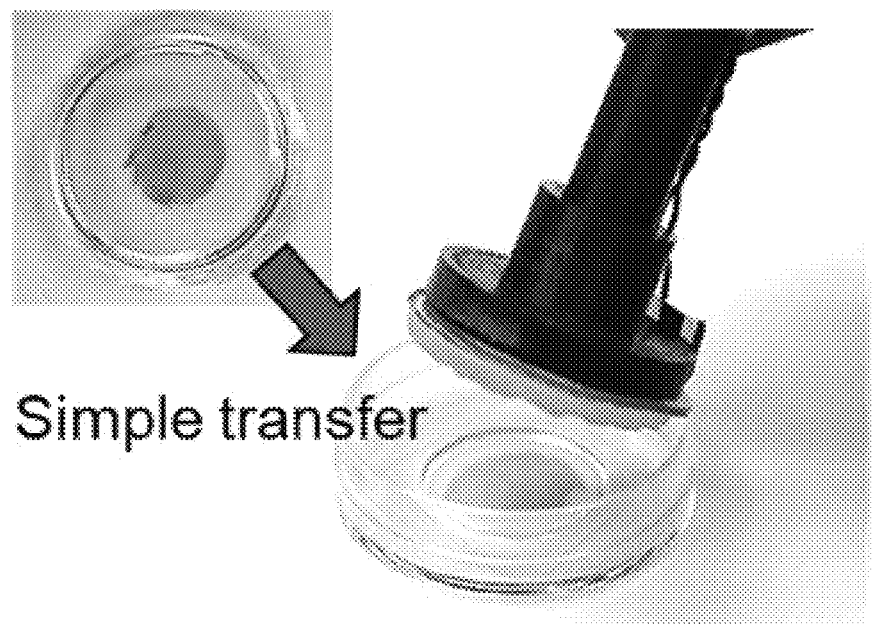
Figure 5C:
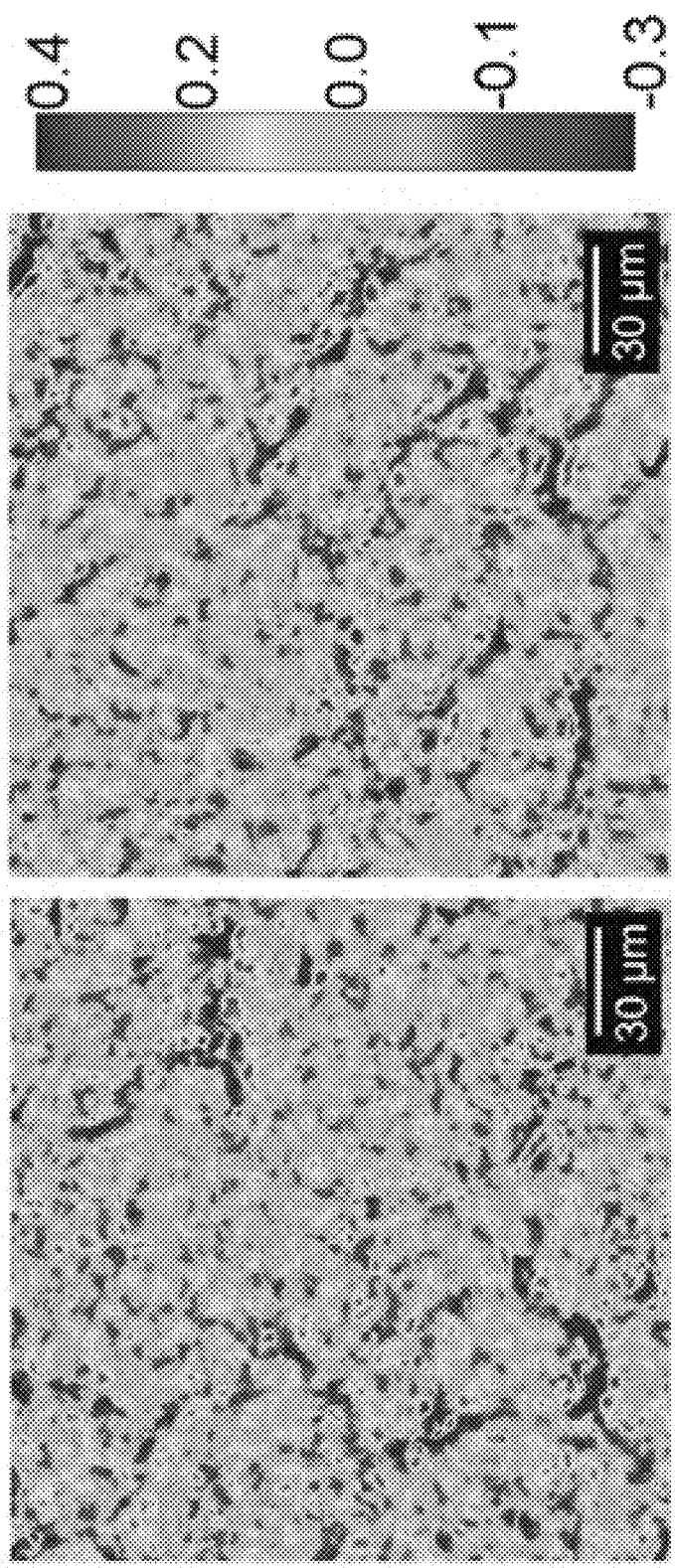
Figure 5D:
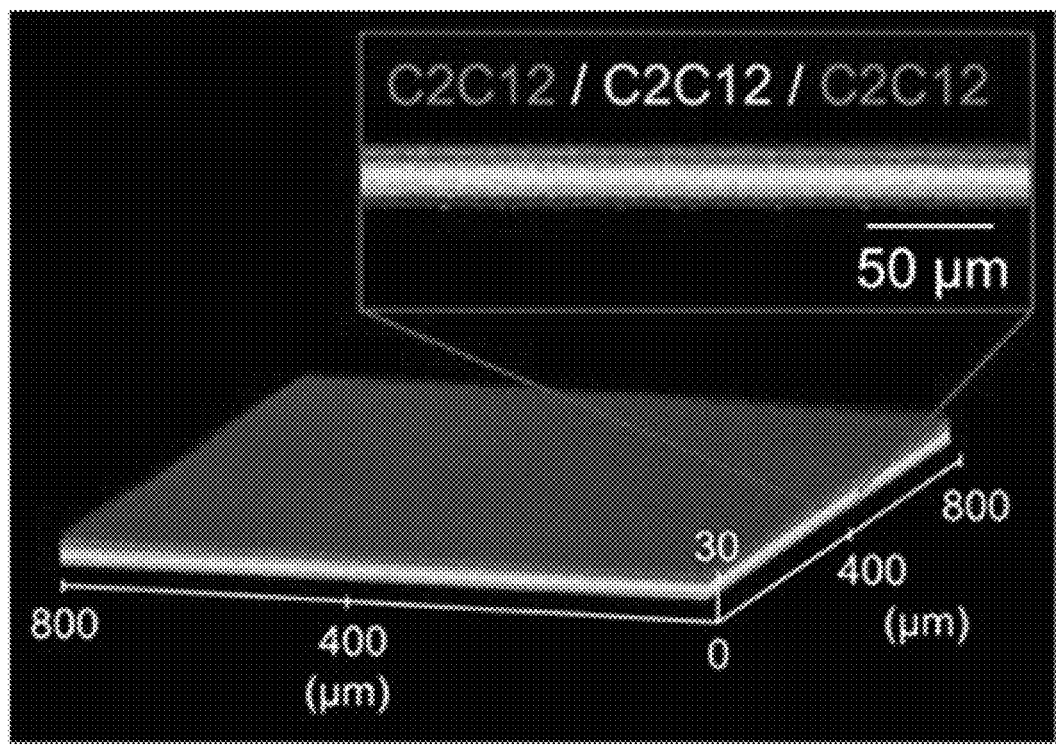
Figure 18A:
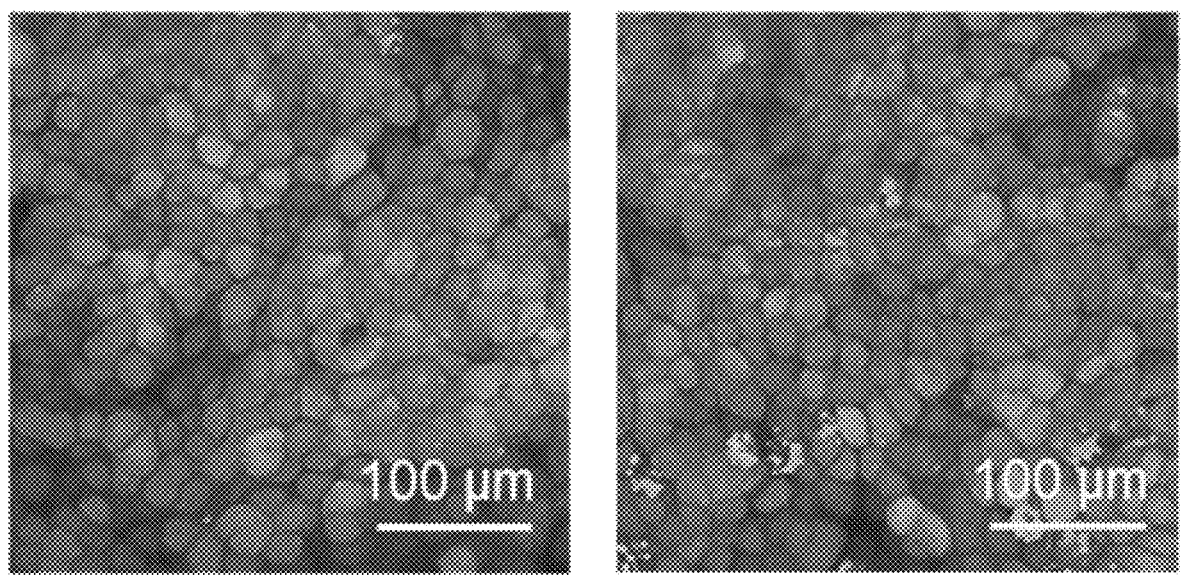
FIGS. 18A-18B: The live-dead assay results of the cell sheet.
Figure 18B:
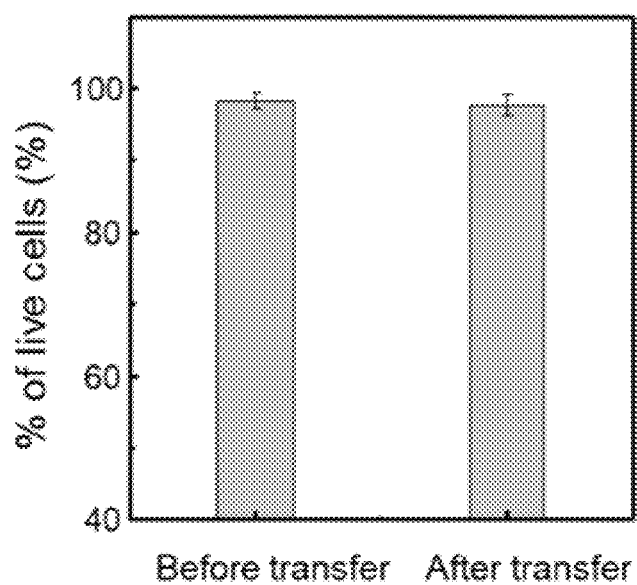

Finally, we examined the capability of the soft manipulator to lift up, transport, and release ultrathin and delicate materials, such as living cell sheets and ultrathin thin film devices. We prepared a single-layered mouse skeletal myoblast cell sheet on a culture dish. In general, monolayered cell sheets were easily damaged or crumpled when picking up the sheet from the cell culture dish with forceps (FIG. 5A). By switching the heater of the soft manipulator on and off, it was possible to lift the myoblast cell sheet and transport them to the new target sites. First, we transferred the cell sheet to a glass dish using the soft manipulator (FIG. 5B). Then, we examined whether the soft manipulator damages the sheet during transplantation. Off-axis deformation and viability of the cell sheet before and after delivering process were measured using the spatial light interference microscopy (SLIM) and the live-dead assay kit, respectively. According to SLIM observation and live-dead assay results, there was no significant wrinkling nor loss of viability of cells that formed the cell sheet during this transport process (FIG. 5C and FIG. 18A-18B). This simple transportation process allowed us to fabricate a 3D tissue by stacking multiple myoblast sheets using the soft manipulator (FIG. 5D). The resulting three-layered myoblast tissue showed a dense construct with three different layers.

Figure 5E:
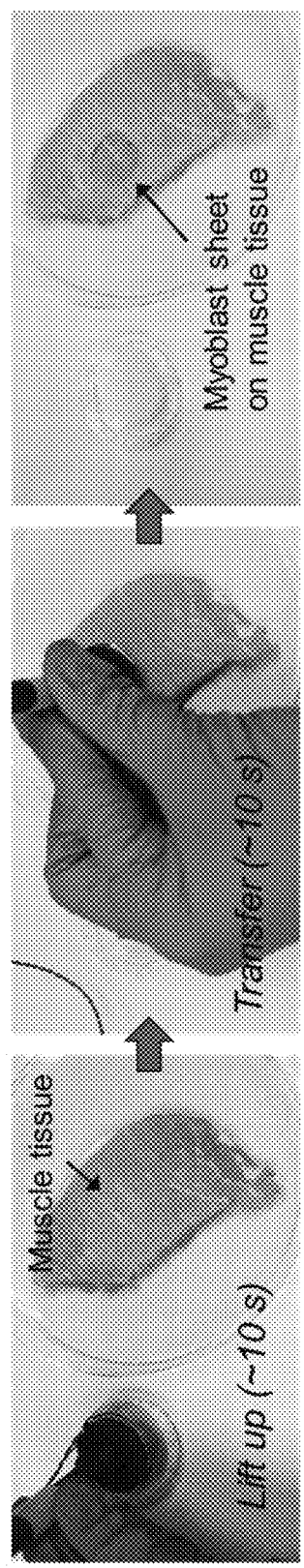
Figure 5F:
Figure 5G:
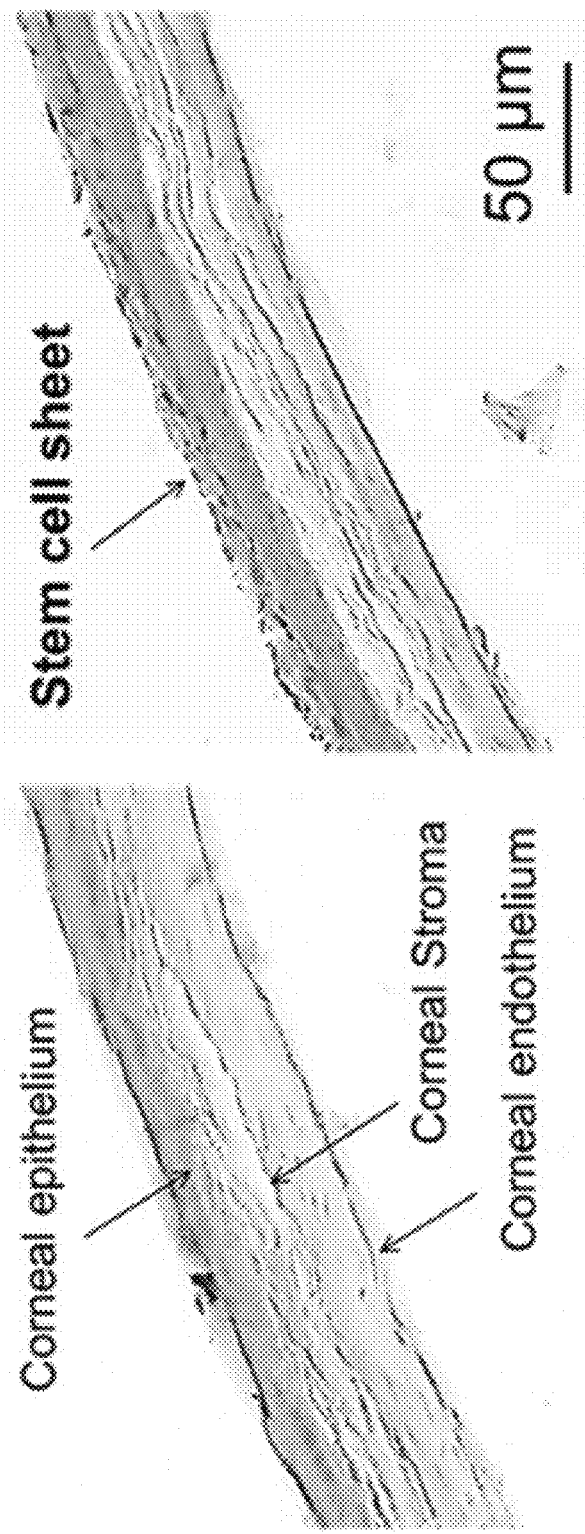
Figure 19:
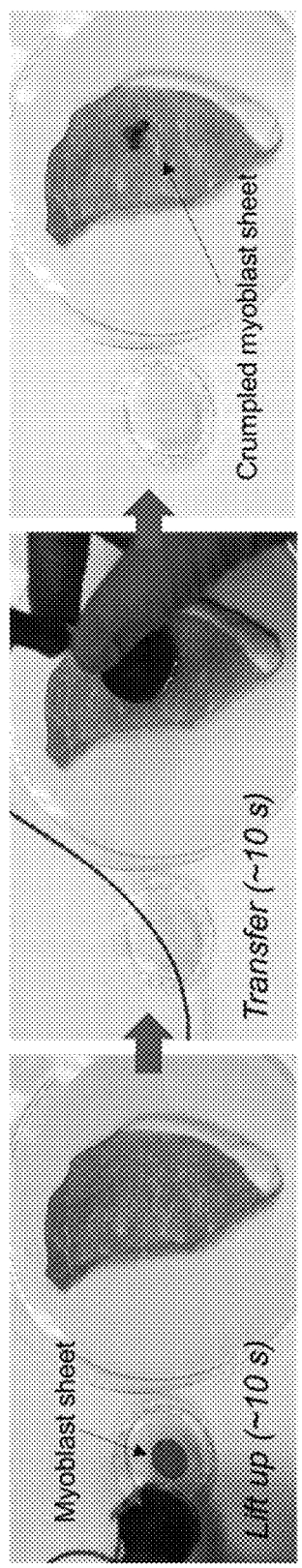
FIG. 19: Snapshots of a process to transport a skeletal myoblast sheet onto a muscle tissue using a soft manipulator made with the gel layer with randomly oriented microchannels.

The soft manipulator allowed us to pick up various types of cell sheets and deliver them rapidly to any target surfaces. As a demonstration, we delivered the myoblast cell sheet to an ex vivo muscle tissue without any structural breakages (FIG. 5E). The entire transport process could be completed within 30 seconds. In contrast, the soft manipulator assembled using a gel with randomly oriented micropores could not uniformly deliver the cell sheet due to the non-uniform micropore shrinkage (FIG. 19). We also used the soft manipulator as a device to support atraumatic transplantation of a stem cell sheet to the anterior surface of the cornea. Similar to the myoblast cell sheet, mesenchymal stem cell sheets on a donor substrate could be easily transferred to the corneal epithelium of a rat eye (FIG. 5F). We confirmed the stable attachment of the stem cell sheet to the anterior surface of the cornea, in the position of the corneal epithelium of the rat eye by histological observation (FIG.

5G). A method to atraumatically transplant ex vivo generated stem cell sheets could simplify surgical technique and expand access to corneal epithelial stem cell transplants and it could have useful application in the treatment of corneal epithelial injuries, persistent epithelial defects, limbal stem cell deficiencies, non-healing corneal ulcers and blast injuries(22, 23).

Figure 6A:
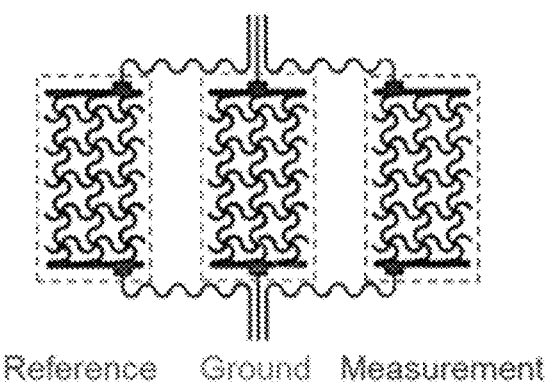
FIG. 6A-6D: Transportation of an ultrathin electrophysiological (EP) sensor.
Figure 6B:
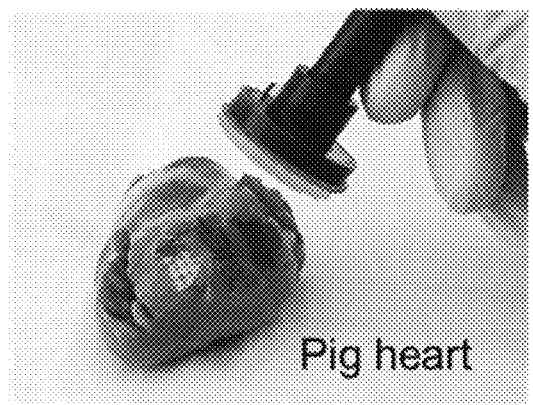
Figure 6C:
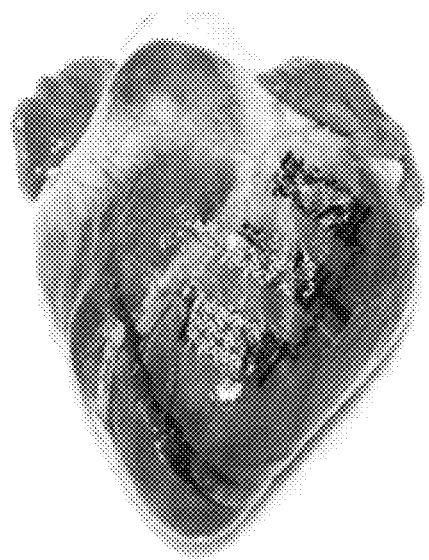
Figure 6D:
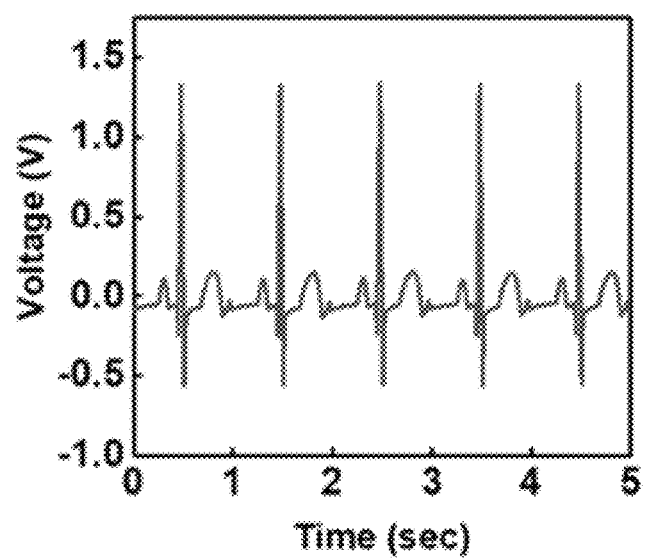
Figure 8A:
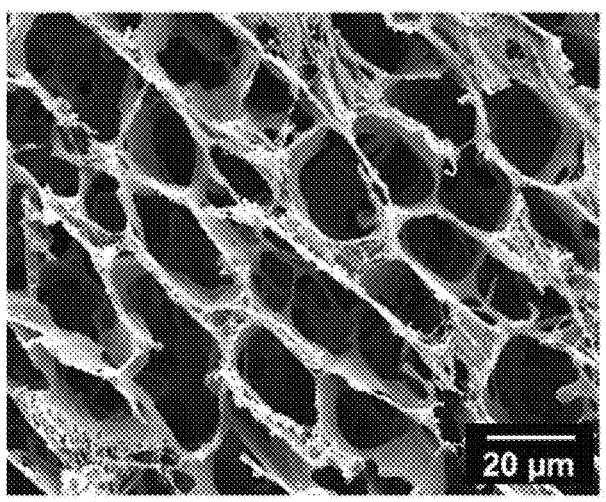
FIG. 8A-8D: SEM images of the gel with directional microchannels before and after shrinkage.
Figure 8B:
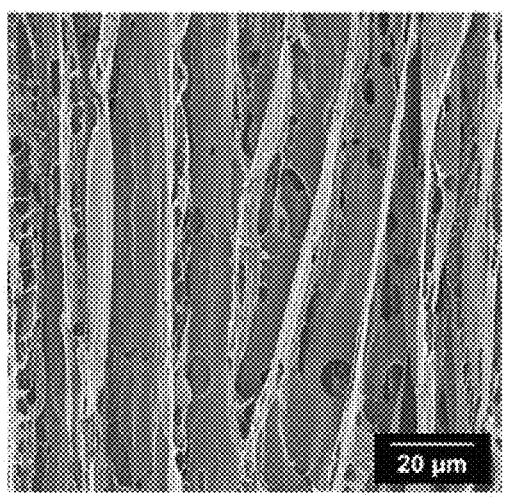
Figure 8C:
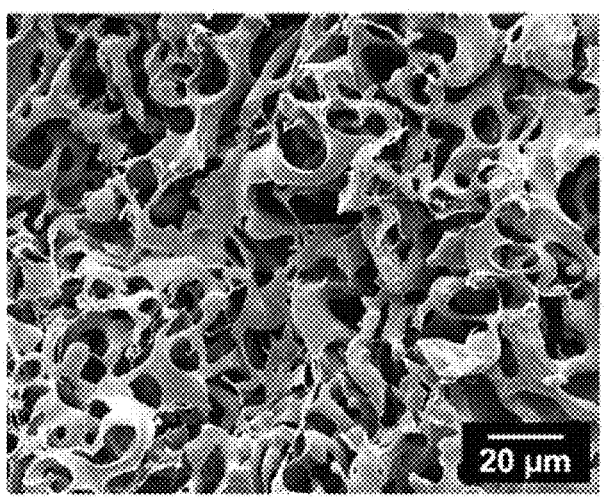
Figure 8D:
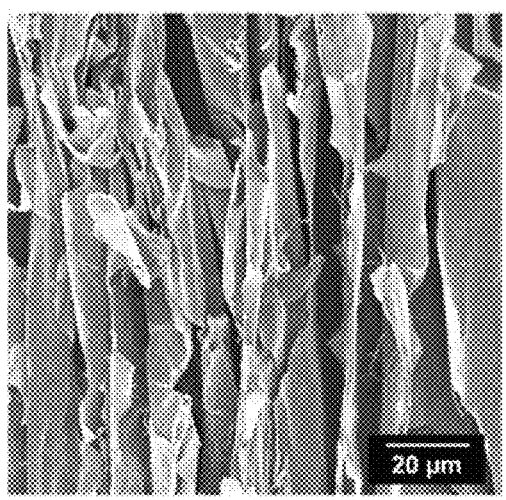
Figure 9A:
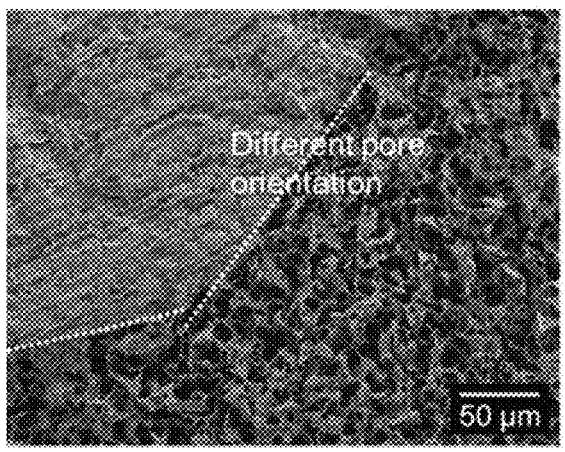
FIG. 9A-9D: SEM images of the gel with randomly oriented microchannels before and after shrinkage.
Figure 9B:
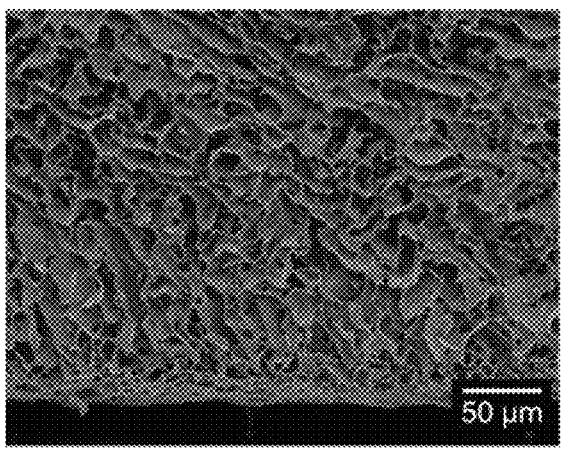
Figure 9C:
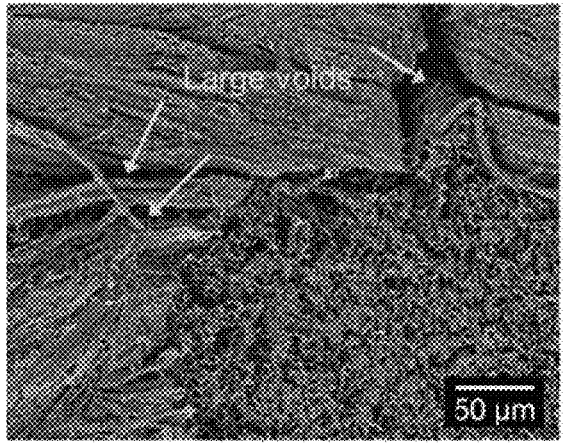
Figure 9D:
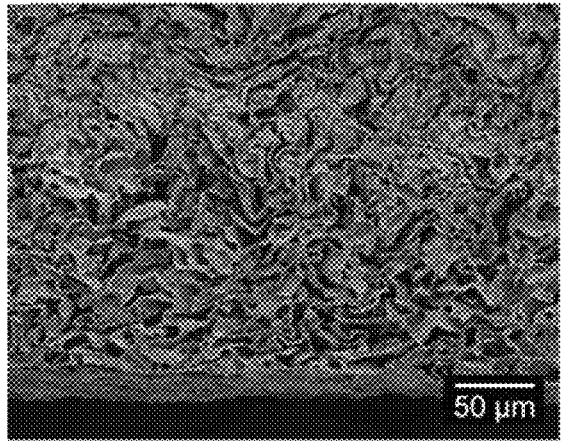
Figure 10A:
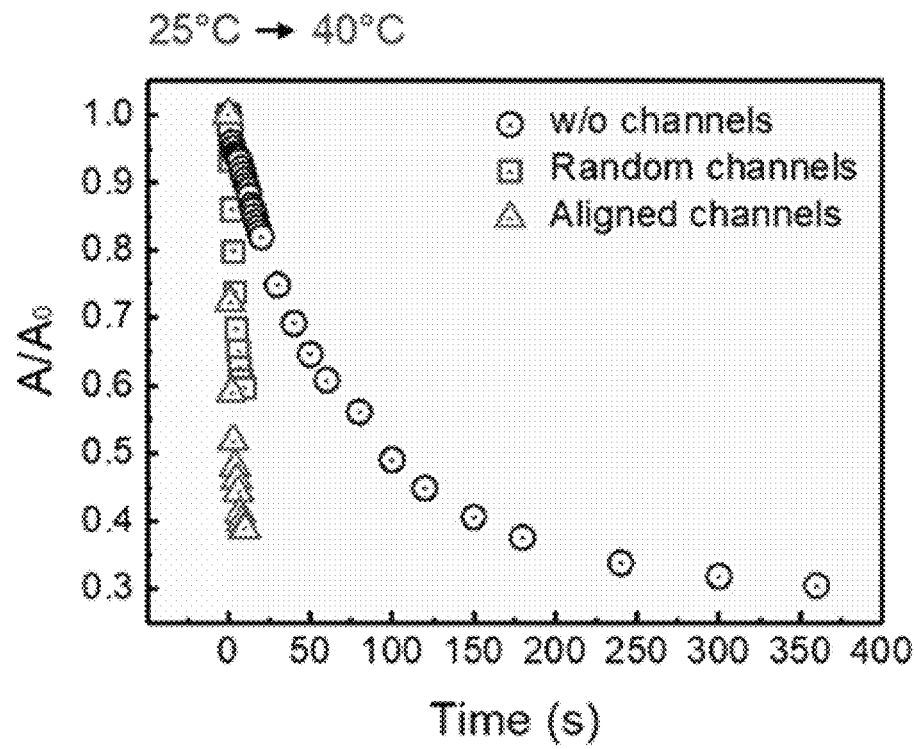
FIGS. 10A-10B: Time-dependent areal changes ($A/A_0$) of the gel without microchannels during heating (FIG. 10A) and cooling (FIG. 10B). The gel samples were placed on a plate at 40° C. or 25° C. The subsequent change in the gel surface area was recorded.
Figure 10B:
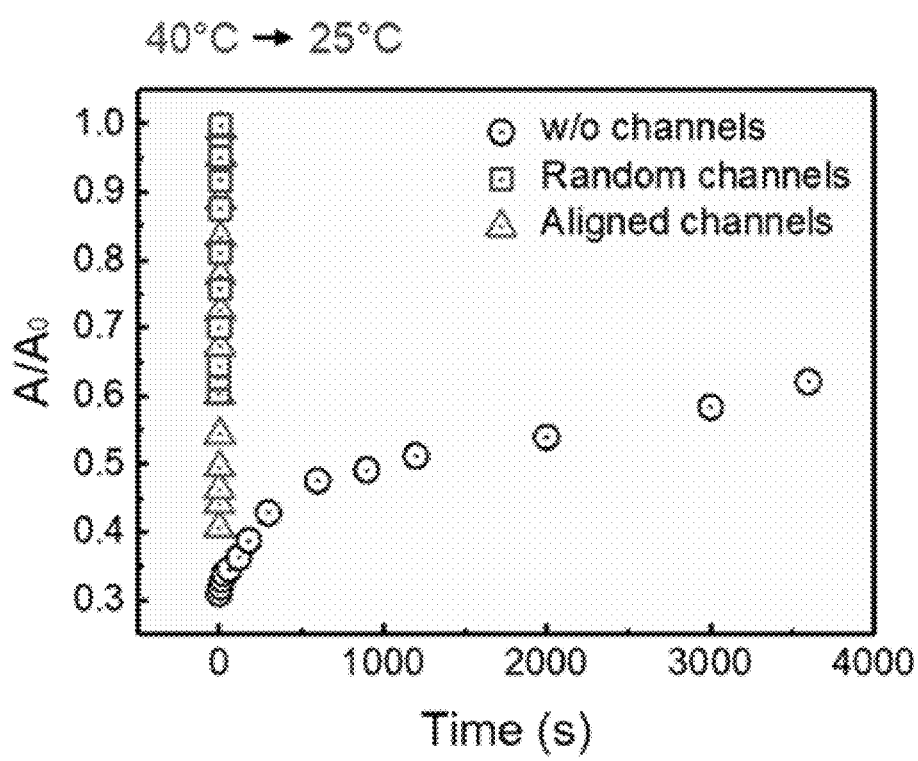
Figure 20:
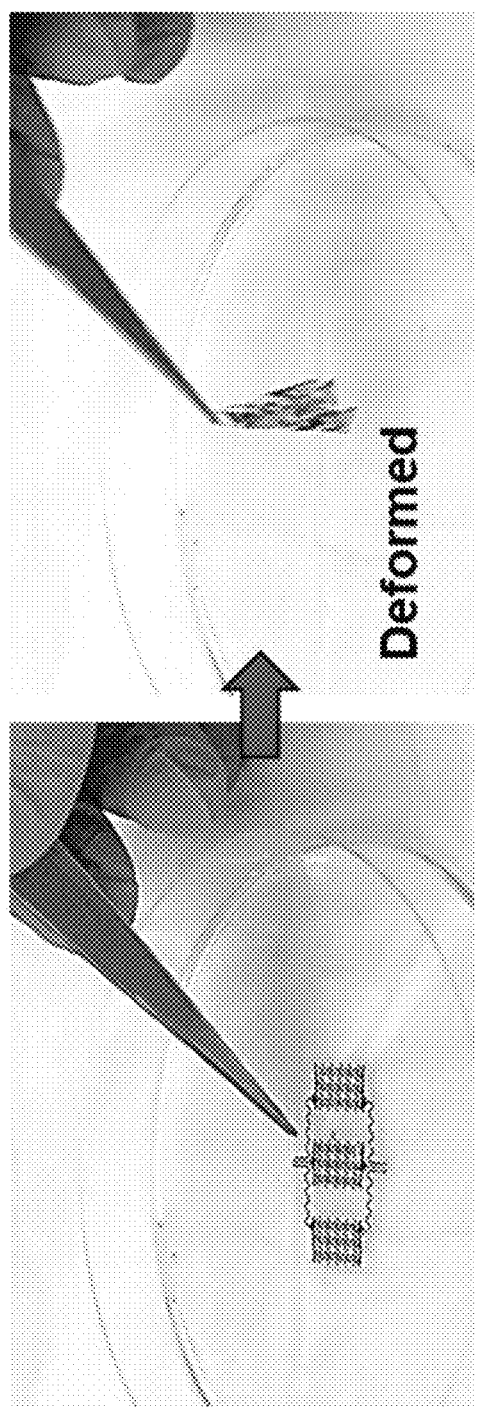
FIG. 20: Snapshots of a process to pick up the ECG device with forceps. The device was deformed when picking up with a forceps (right).
Figure 21A:
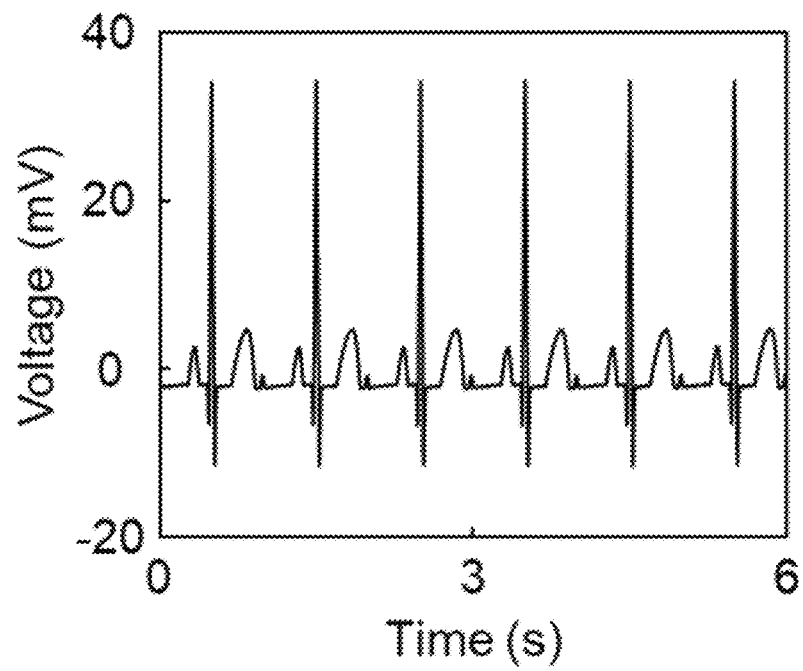
FIGS. 21A-21B: Representative input and output ECG signals.
Figure 21B:
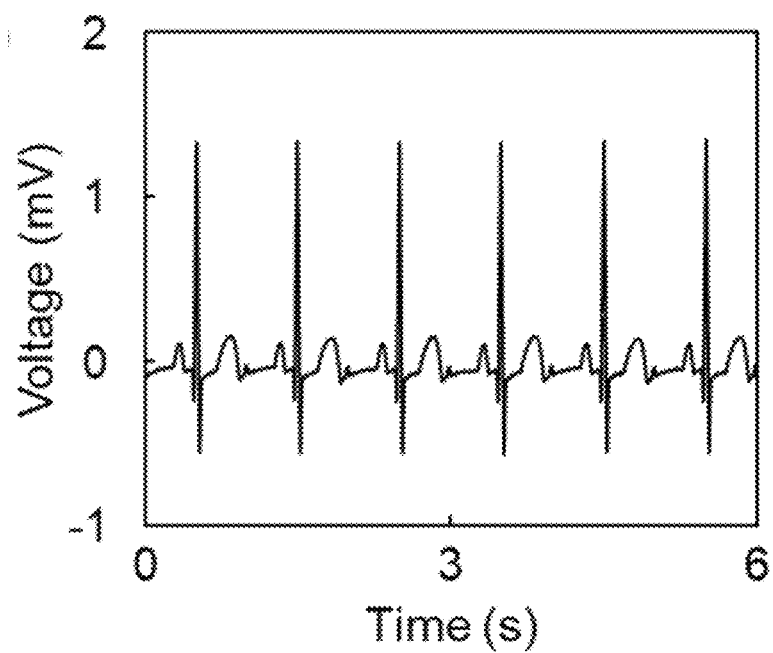

Also, the soft manipulator was used to transport an ultrathin electrophysiological (EP) sensor (thickness: ~1 μm) without causing wrinkling. We fabricated the EP sensor that consists of reference, ground, and measurement electrodes allowing for high-quality recording of electrocardiogram (ECG) signals (FIG. 6A)(24, 25). Generally, such ultrathin film devices were easily crumpled when picking up from a donor substrate, which typically requires the use of a temporary handling support (FIG. 20). By using the soft manipulator, it was possible to controllably transfer the EP sensor from the donor substrate to the surface of the pig heart within a minute (FIG. 6B). No substantial wrinkles were observed after completing the transport (FIG. 6C). A waveform generator was used to apply a preprogrammed ECG signals across the pig heart using an Ag/AgCl electrode. The resulting ECG signals captured from the EP sensor was nearly identical to those generated from the waveform generator (FIG. 6D and FIG. 21A-21B). The Pearson's correlation coefficient of the signals was 0.98.

Taken together, this example demonstrates that the soft manipulator assembled by integrating a rapid thermal-responsive microchanneled gel and an electrothermal heater can transport ultrathin biological and electronic materials quickly and safely. The resulting soft manipulator could be switched on and off with electricity to lift and release thin and delicate materials within tens of seconds. This rapid handling could be attained with the electrothermally controlled change in the adhesion force between the soft manipulator and target materials. Such an actuation mechanism is very similar to the muscular action of cephalopod suction cups. Therefore, this soft manipulator is distinct from previous suction cup-mimicking platforms that need external force for detachment of materials. In addition, the soft manipulator could move thin materials of interest in both wet and dry conditions. Using this unique functionality, we can assemble multi-layered cell sheets and place an ultrathin biosensor to the target tissue without impairing its function.

Further modification of this soft manipulator with an electronic sensor would allow robots to transport ultrathin materials autonomously. For instance, the resulting, smart soft manipulator would be able to monitor the degree of deformation of transporting materials during contact and, in turn, adjust the suction force to a level at which materials retain their structural integrity and functionality. By doing so, the soft manipulator would improve its performance from the standpoint of safety and accuracy of material handling and assembly. The instant manipulators have a range of applications, as they are widely compatible as a new soft handling tool for the fabrication of ultrathin film devices, tissue engineering, and transplant surgery.

This example demonstrates an electrically controllable soft machinery useful to transport ultrathin, delicate objects, including therapeutic cell sheets and thin, wearable biosensing devices. This system, referred to as the electrothermal soft manipulator, comprises a flexible heater attached with a rapid thermo-responsive PNIPAAm hydrogel disk with controlled microchannel architecture and tissue-like softness. Compared with hydrogels free of microchannels or those with randomly oriented microchannels, the anisotropically aligned PNIPAAm hydrogel could shrink and expand in response to the electrically induced heat much faster, on the order of seconds. Such a fast-volumetric change of the microchannels on the surface of an object could produce and remove pressure-induced adhesion repeatedly. This controlled actuation mechanism is similar to the activity of cephalopod suction cups that hold and release objects of interest using bioelectric signals. As a consequence, the soft manipulator can move thin biological and bioelectronic devices quickly in both wet and dry conditions without causing wrinkling or damage of the thin materials. Such an electrothermally controlled soft manipulator is useful for various applications that require the sophisticated manipulation of fragile and delicate biological tissues and bioelectronic devices.

MATERIALS AND METHODS: Preparation of the microchanneled PNIPAAm gel. 1.25 g of NIPAAm and 12.5 mg (0.01 wt % of NIPAAm) of N, N'-Methylenebisacrylamide were dissolved in distilled water (8.75 mL) for 1 day at 25° C. to ensure the complete dissolution. Then, 25 mg (0.5 wt % of NIPAAm) of radical photo-initiator (Irgacure 2959) was added into the obtained solution and stirred until all the solids completely dissolved. The resulting pre-gelled NIPAAm solution was poured onto a Si-wafer substrate (4-inch, 550 μm thick) with silicone mold (50×50×1 mm or 20×20×10 mm). Then, the Si-wafer substrate was put on a liquid nitrogen reservoir for the directional crystallization of the pre-gelled NIPAAm solution. The distance between the bottom surface of the Si-wafer and the top surface of liquid nitrogen was 1 cm. After complete crystallization of the pre-gelled NIPAAm solution, the samples were irradiated with a UV lamp (λ=365 nm) for 6 hrs at a −25° C. freezer for the radical cryo-polymerization. The as-prepared poly-NIPAAm gel (PNIPAAm) was then washed with fresh water three times to remove the ice crystals.

For comparison, PNIPAAm gel with randomly oriented microchannels was prepared by placing the pre-gelled NIPAAm solution in a freezer at −25° C. for random crystallization. Then, the resultant samples were cryo-polymerized and washed at the same condition described above. PNIPAAm gel free of microchannels was prepared by skipping the crystallization and subsequently irradiated with a UV lamp for 1 h at 4° C. All hydrogel samples were soaked in 250 mL distilled water at 25° C., which was repeatedly replaced for 1 day to remove unreacted impurities before using them.

Characterization of PNIPAAm gels. The morphology of microchanneled PNIPAAm gels were examined using an environmental scanning electron microscope (ESEM, Quanta FEG 450, FEI) and micro-computed tomography (micro-CT, MicroXCT-200, Xradia Inc.). For cross-sectional analysis, the samples were immersed in liquid nitrogen for 30 min and immediately cryo-fractured. One hundred points from ten different ESEM images were taken to determine the average pore size. The porosity of gels was determined by the gravimetric method. The pore volume of gels was divided by the total volume of gels as follows:

$$\text{Porosity (\%)} = \{(W_{swollen} - W_{dry})/\rho_w\} / \{(W_{swollen} - W_{dry})/\rho_w + (W_{dry}/\rho_{PNIPAAm})\} \quad (3)$$

where $W_{swollen}$ and $W_{dry}$ are the weights of swollen and dry gels, respectively, pw is the water density, and $\rho_{PNIPAAm}$ is the NIPAAm density (1.1 g/cm³).

For equilibrium swelling ratio (ESR) measurement, we measured the weight of PNIPAAm gels at different temperatures (4-40° C.) with 4° C. increments. The equilibrium swelling ratio was defined using the following equation:

$$ESR(\%) = \{(W_s - W_d)/W_d\} \cdot 100 \quad (4)$$

The hydrogel samples were equilibrated at each temperature for 12 hrs and weighted ($W_s$) after removing excess water. The dry weight of the samples ($W_d$) was measured after lyophilization. Five samples of each PNIPAAm gel were averaged.

For dynamic deformation analysis of hydrogels in response to temperature change, hydrogel samples immersed in 25° C. were trimmed into a cylinder shape (d=25 mm, t=1 mm) and placed on a copper plate (t=1 mm). Then, the plate was put onto a heated Peltier stage (40° C.) to investigate the de-swelling kinetics of samples. For re-swelling kinetics, de-swelled samples were transferred to a cooled Peltier stage (25° C.). We monitored the volume change in response to temperature using an optical microscope that connected with the Peltier device (TP104SC-mK2000A, Instec.). All-optical images were analyzed using Image-J software.

The compressive modulus of hydrogels was measured on an electronic universal testing machine (Instron 5943, Instron) equipped with a water bath. Samples were cut into a square shape (10×10×10 mm). All mechanical tests were conducted in a water bath (25° C.). There were five replicates for all mechanical tests.

Preparation of the flexible (Joule) heater. The heater was fabricated on a copper/polyimide film (t=9 μm/12 μm, Pyralux™ AC091200EV, Dupont). A standard photolithographic patterning with a dry film photoresist (Riston MM540, Dupont) followed by the wet etching method (CE-100, Transene, Inc.) defined the copper layer into a joule heating element. The copper traces were coated with 1 μm layer of tin (Sn) (421 Liquid Tin, MG Chemicals) to protect the copper from oxidation in elevated temperatures within a humid environment. The resulting heater was then connected to an external power supply where a voltage range of 2-5 V and its thermal characterizations over time were recorded using an infrared camera (E40, FLIR Systems).

Fabrication of the soft manipulator. The cyanoacrylate-based adhesive was spread on top of the flexible heating array(21). Immediately after, the hydrogel was trimmed into a cylinder shape (d=25 mm, t=1 mm) and pressed onto the substrate. The bonding occurs within 30 seconds. The resulting gel/heater was attached to a 3D printed supporter using double-sided tape (VHB, 3M). Then, the soft manipulator was connected to an electrical power supply.

Characterization of the soft manipulator. For dynamic deformation analysis of the soft manipulator in response to activation of a heater, a monochrome camera (DS-Qi2, Nikon) was attached to an optical microscope (Eclipse LV100, Nikon) for top-view analysis of the gel in the soft manipulator. A digital camera with an optical zoom macro lens (Canon, MP-E 65 mm) was used for the side-view analysis of the soft manipulator. Gels in the soft manipulator were incubated with colored water (Green, McCormick) for visualization of water.

Adhesion tests were performed with a dynamic mechanical analyzer (DMA, ESM303, Mark-10). The soft manipulator was mounted on a load cell of the DMA (M5-5 or M5-200, Mark-10), and the vertical approach and retraction speeds of the soft manipulator were 0.1 mm/s. Force-displacement profiles with time were measured at room temperature.

To examine the capability of the soft manipulator to handling materials with different elastic moduli, alginate hydrogels with elastic moduli of 23 and 70 kPa were used in this study. Pre-gelled alginate solution was prepared by mixing 2 wt % alginate solution in (N-morpholino)ethane-sulfonic acid (MES buffer, pH=6.5) with sulfonated N-hydroxysuccimide (Sulfo-NHS) and 1-ethyl-3-(3-dimethyl-aminopropyl) carbodiimide (EDC). Then, the pre-gelled alginate solution was cross-linked by adding adipic acid dihydrazide (AAD). The elastic modulus of the alginate gels was controlled by varying the molar ratio between AAD and uronic acids of alginate (MAAD).

Cross-sectional fluorescence images were obtained from 3D z-stack confocal images (LSM 880, Carl Zeiss). We used Rhodamine B mixed with water for tracking of water inside the soft manipulator before and after the attachment process.

To investigate surface contamination of the soft manipulator, we performed adhesion tests to silicon wafers using either the soft manipulator or a commercial medical grade tape (Transpore™, 3M). After detachment of the samples, the resulting wafer was incubated with a dye (Rhodamine B) for 30 min. All samples were washed with distilled water three times in total. Then, we dried the wafer surface using $N_2$ gas and subsequently observed the wafer surfaces using fluorescent optical microscopy.

Preparation of stem cell sheets. C2C12 cells (mouse skeletal myoblast cell line, CRL1772) and D1 cells (bone marrow-derived mesenchymal stem cell line, CRL12424) were obtained from American Type Cell Culture (ATCC). C2C12 or D1 cells were plated on temperature-responsive PNIPAAm-grafted culture dishes (d=35 mm, UpCell™, Thermo Scientific) with seeding density of 5×105 cells). The cells were then cultivated for 3 days according to the guidelines of ATCC. To harvest sheets, confluent cells were rinsed twice with warmed Dulbecco's Phosphate-Buffered Saline (DPBS). Then, the monolayers were detached from the culture dish by lowering the incubation temperature from 37° C. to 20° C.

Analysis of cell sheets after transport using the soft manipulator. The viability of cell sheets was examined using LIVE/DEAD® Viability/Cytotoxicity Assay Kit for mammalian cells (Invitrogen) according to the manufacturer's instructions. The cultured cells or transferred cells were gently washed 3 times with DPBS. Calcein Acetoxymethyl (AM) and ethidium homodimer-1 (EthD-1) were diluted together in DPBS. 1 mL of diluted Calcein AM and EthD-1 solution was added to cultured cells and kept for 45 min at room temperature. The live cells were stained with Calcein-AM, and dead cells were stained with EthD-1. After staining, cells were gently washed with 1×DPBS for three times and imaged with a fluorescence microscope (LSM-880, Carl Zeiss). Off-axis deformation of the cell sheets before and after the delivery process was quantified using spatial light interference microscopy (SLIM). The optical system was assembled by attaching a SLIM module (CellVista SLIM pro, Phi Optics) to the output port of an existing inverted phase-contrast microscope(26).

Assembly of a multi-layered cell sheet using the soft manipulator. C2C12 cells were cultured onto a temperature-responsive culture dish to produce cell sheets as described above. After incubation, confluent cells were stained with Cell Tracker Orange CMRA (Invitrogen) or Calcein-AM (Invitrogen). Then, cell sheets were detached from the culture dish by lowering the incubation temperature from 37° C. to 20° C. The detached cell sheets were captured and transferred using the soft manipulator with electrical heater control. A multi-layered cell sheet was fabricated by repeating the transfer procedure. The resulting, multi-layered tissue structure was imaged using a fluorescence microscope (LSM-880, Carl Zeiss).

Transplantation of a stem cell sheet onto the anterior surface of the cornea using the soft manipulator. Long-Evans/BluGill rats were used in this study. All experimental protocols were in compliance with the National Institutes of Health Public Health Service Policy on Humane Care and Use of Laboratory Animals and were approved by the UIUC Institutional Animal Care and Use Committee. For fixation of the cornea, the perfusion needle was inserted into the left ventricle of the heart. A cut was made within the right atrium to allow for blood evacuation. Saline was injected at a rate of 300 ml/min to clear the blood from the rat, followed by injection of paraformaldehyde (PFA) at 300 ml/min. The perfusion was confirmed by checking PFA dripping from the nose of the rate, stiffening of the extremities and the liver, and contractures of the musculature. After completing the perfusion, the stem cell sheet was placed on the rat's cornea using the soft manipulator. The other rat eye was used as a control. Enucleation was then performed using micro-scissors.

Immunohistochemistry and imaging of the stem cell sheet transplanted on the cornea. Enucleation was followed by placement of the eyeball on dry ice then into a mold. The mold was subsequently filled with an optimal cutting temperature (OCT) compound-embedding medium to ensure optimal cutting temperature. Cryosectionning at 40 µm slices was performed using a cryostat. Slices were then fixed using 4% PFA since the eyeball was fixed but not the stem cell sheet. The sample was washed 3 times in TBS for 5 minutes. The section was stained with Hematoxylin and Eosin staining, followed by dehydration in citrasol for 5 minutes. The stained tissue section was imaged using the Axiozoom V16.

Fabrication of the electrophysiological (EP) sensor and evaluation of its function after placement onto an ex vivo heart using the soft manipulator. The fabrication of the EP sensor began by spin-coating a layer of poly(methyl methacrylate) (PMMA, ~1 µm thick) on a glass substrate, followed by thermal annealing at 180° C. for 1 minute. A subsequent layer of polyimide (~1 µm thick) was coated and cured in a vacuum oven at 250° C. for 1 hour. Thin films of Cr and Au (t=5 nm/150 nm thick) were deposited by using an electron beam evaporation. Photolithographic patterning using a negative-type photoresist (Riston MM540, DuPont) followed by a wet etching with Au and Cr etchants (Transene) defined the Joule-heating element. The resulting structure was submerged in acetone to dissolve the bottom PMMA layer. An anisotropic conductive film (ACF, HST-9805-210, Elform) was bonded to the terminals and was connected to an external data acquisition system. The measurement of ECG signals began by attaching two commercial conducting electrodes (30 mm×24 mm, H124SG, Kendall) diagonally across the pig heart. The electrodes were then connected to an arbitrary waveform generator (3390, Keithley) to apply a preprogrammed cardiac waveform (1 Hz frequency, 50 mV amplitude). The EP sensor was transferred onto the surface of the pig heart with the soft manipulator. The sensor was connected to an external preamplifier (Octal Bio Amp, ADInstruments) and data acquisition unit (PowerLab 16/35, ADInstruments) where the captured ECG signal was digitally filtered with a bandpass filter at the bandwidth of 0.5-100 Hz

REFERENCES FOR EXAMPLE 1

1. J. Yang, M. Yamato, C. Kohno, A. Nishimoto, H. Sekine, F. Fukai, T. Okano, Cell sheet engineering: Recreating tissues without biodegradable scaffolds. Biomaterials. 26, 6415-6422 (2005).
2. J. Yang, M. Yamato, T. Shimizu, H. Sekine, K. Ohashi, M. Kanzaki, T. Ohki, K. Nishida, T. Okano, Reconstruction of functional tissues with cell sheet engineering. Biomaterials. 28, 5033-5043 (2007).
3. K. Nishida, M. Yamato, Y. Hayashida, K. Watanabe, N. Maeda, H. Watanabe, K. Yamamoto, S. Nagai, A. Kikuchi, Y. Tano, T. Okano, Functional bioengineered corneal epithellial sheet grafts from corneal stem cells expanded ex vivo on a temperature-responsive cell culture surface. Transplantation. 77, 379-385 (2004).
4. H. Sekine, T. Shimizu, K. Sakaguchi, I. Dobashi, M. Wada, M. Yamato, E. Kobayashi, M. Umezu, T. Okano, In vitro fabrication of functional three-dimensional tissues with perfusable blood vessels. Nat. Commun. 4, 1-10 (2013).
5. D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, Epidermal Electronics. Science. 333, 838-843 (2011).
6. D.-H. Kim, R. Ghaffari, N. Lu, S. Wang, S. P. Lee, H. Keum, R. D'Angelo, L. Klinker, Y. Su, C. Lu, Y.-S. Kim, A. Ameen, Y. Li, Y. Zhang, B. de Graff, Y.-Y. Hsu, Z. Liu, J. Ruskin, L. Xu, C. Lu, F. G. Omenetto, Y. Huang, M. Mansour, M. J. Slepian, J. A. Rogers, Electronic sensor and actuator webs for large-area complex geometry cardiac mapping and therapy. Proc. Natl. Acad. Sci. 109, 19910-19915 (2012).
7. L. Tian, B. Zimmerman, A. Akhtar, K. J. Yu, M. Moore, J. Wu, R. J. Larsen, J. W. Lee, J. Li, Y. Liu, B. Metzger, S. Qu, X. Guo, K. E. Mathewson, J. A. Fan, J. Cornman, M. Fatina, Z. Xie, Y. Ma, J. Zhang, Y. Zhang, F. Dolcos, M. Fabiani, G. Gratton, T. Bretl, L. J. Hargrove, P. V Braun, Y. Huang, J. A. Rogers, Large-area MRI-compatible epidermal electronic interfaces for prosthetic control and cognitive monitoring. Nat. Biomed. Eng. 3, 194-205 (2019).
8. J.-W. Jeong, W.-H. Yeo, A. Akhtar, J. J. S. Norton, Y.-J. Kwack, S. Li, S.-Y. Jung, Y. Su, W. Lee, J. Xia, H. Cheng, Y. Huang, W.-S. Choi, T. Bretl, J. A. Rogers, Materials and Optimized Designs for Human-Machine Interfaces Via Epidermal Electronics. Adv. Mater. 25, 6839-6846 (2013).
9. S. De, J. Rosen, A. Dagan, B. Hannaford, P. Swanson, M. Sinanan, Assessment of Tissue Damage due to Mechanical Stresses. Int. J. Rob. Res. 26, 1159-1171 (2007).
10. A. Carlson, A. M. Bowen, Y. Huang, R. G. Nuzzo, J. A. Rogers, Transfer Printing Techniques for Materials Assembly and Micro/Nanodevice Fabrication. Adv. Mater. 24, 5284-5318 (2012).
11. X. Liang, B. A. Sperling, I. Calizo, G. Cheng, C. A. Hacker, Q. Zhang, Y. Obeng, K. Yan, H. Peng, Q. Li, X. Zhu, H. Yuan, A. R. Hight Walker, Z. Liu, L. Peng, C. A. Richter, Toward Clean and Crackless Transfer of Graphene. ACS Nano. 5, 9144-9153 (2011).
12. Z. Yan, T. Pan, M. Xue, C. Chen, Y. Cui, G. Yao, L. Huang, F. Liao, W. Jing, H. Zhang, M. Gao, D. Guo, Y. Xia, Y. Lin, Thermal Release Transfer Printing for Stretchable Conformal Bioelectronics. Adv. Sci. 4, 1700251 (2017).
13. S. Baik, D. W. Kim, Y. Park, T. J. Lee, S. Ho Bhang, C. Pang, A wet-tolerant adhesive patch inspired by protuberances in suction cups of octopi. Nature. 546, 396-400 (2017).

14. H. Lee, D.-S. Um, Y. Lee, S. Lim, H. Kim, H. Ko, Octopus-Inspired Smart Adhesive Pads for Transfer Printing of Semiconducting Nanomembranes. Adv. Mater. 28, 7457-7465 (2016).
15. M. K. Choi, O. K. Park, C. Choi, S. Qiao, R. Ghaffari, J. Kim, D. J. Lee, M. Kim, W. Hyun, S. J. Kim, H. J. Hwang, S. H. Kwon, T. Hyeon, N. Lu, D. H. Kim, Cephalopod-Inspired Miniaturized Suction Cups for Smart Medical Skin. Adv. Healthc. Mater. 5, 80-87 (2016).
16. W. M. Kier, A. M. Smith, The structure and adhesive mechanism of octopus suckers. Integr. Comp. Biol. 42, 1146-1153 (2002).
17. F. Tramacere, L. Beccai, M. Kuba, A. Gozzi, A. Bifone, B. Mazzolai, The Morphology and Adhesion Mechanism of Octopus vulgaris Suckers. PLoS One. 8, e65074 (2013).
18. J. Kim, Y. Cho, S. Kim, J. Lee, 3D Cocontinuous Composites of Hydrophilic and Hydrophobic Soft Materials: High Modulus and Fast Actuation Time. ACS Macro Lett. 6, 1119-1123 (2017).
19. H. Bai, A. Polini, B. Delattre, A. P. Tomsia, Thermoresponsive composite hydrogels with aligned macroporous structure by ice-templated assembly. Chem. Mater. 25, 4551-4556 (2013).
20. P. Gao, P. R. Nixon, J. W. Skoug, Diffusion in HPMC Gels. II. Prediction of Drug Release Rates from Hydrophilic Matrix Extended-Release Dosage Forms. Pharm. Res. 12, 965-971 (1995).
21. D. Wirthl, R. Pichler, M. Drack, G. Kettlguber, R. Moser, R. Gerstmayr, F. Hartmann, E. Bradt, R. Kaltseis, C. M. Siket, S. E. Schausberger, S. Hild, S. Bauer, M. Kaltenbrunner, Instant tough bonding of hydrogels for soft machines and electronics. Sci. Adv. 3, 1-10 (2017).
22. N. Tananuvat, K. Bumroongkit, C. Tocharusa, U. Mevatee, A. Kongkaew, S. Ausayakhun, Limbal stem cell and oral mucosal epithelial transplantation from ex vivo cultivation in LSCD-induced rabbits: histology and immunologic study of the transplant epithelial sheet. Int. Ophthalmol. 37, 1289-1298 (2017).
23. P. Prabhasawat, P. Ekpo, M. Uiprasertkul, S. Chotikavanich, N. Tesavibul, K. Pornpanich, P. Luemsamran, Long-term result of autologous cultivated oral mucosal epithelial transplantation for severe ocular surface disease. Cell Tissue Bank. 17, 491-503 (2016).
24. S. Han, M. K. Kim, B. Wang, D. S. Wie, S. Wang, C. H. Lee, Mechanically Reinforced Skin-Electronics with Networked Nanocomposite Elastomer. Adv. Mater. 28, 10257-10265 (2016).
25. J.-W. Jeong, M. K. Kim, H. Cheng, W. H. Yeo, X. Huang, Y. Liu, Y. Zhang, Y. Huang, J. A. Rogers, Capacitive epidermal electronics for electrically safe, long-term electrophysiological measurements. Adv. Healthc. Mater. 3, 642-648 (2014).
26. Z. Wang, L. Millet, M. Mir, H. Ding, S. Unarunotai, J. Rogers, M. U. Gillette, G. Popescu, Spatial light interference microscopy (SLIM). Opt. Express. 19, 1016-1026 (2011).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of components are intended to be exemplary, as it is known that one of ordinary skill in the art can name the same components differently.

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A manipulator comprising:
   a contact layer having a contact surface with thermally responsive recess features;
   a microelectric heater in thermal contact with the contact surface;
   an electrical power source electrically connected to the microelectric heater;
   wherein the thermally responsive recess features have:
   a thermally actuated geometry with microelectric heater actuation; and
   a thermally relaxed geometry without microelectric heater actuation,
   wherein the thermally actuated geometry is different than the thermally relaxed geometry.

2. The manipulator of claim 1, wherein the contact layer comprises a polymeric hydrogel or an elastomer.

3. The manipulator of claim 1, wherein the contact layer:
   is soft with an anisotropic elastic modulus less than or equal to 10 kPa, with the elastic modulus in a direction perpendicular to an alignment direction of the recess features that is 1.5 to 2.5 times lower than the elastic modulus in a direction parallel to the alignment direction of the recess features;
   has an average thickness that is greater than or equal to 100 µm and less than or equal to 1 cm;
   has a footprint that is greater than or equal to 10 mm$^2$ and less than or equal to 350 cm$^2$;
   has a thermal responsivity that is equal to or less than 10 seconds;
   has a recess feature porosity of between 90% and 98%; and/or
   has recess features that are aligned microchannels with an average channel diameter of between 0.1 µm and 500 µm.

4. The manipulator of claim 1, further comprising: an adhesive layer positioned between the contact layer and the microelectric layer to adhere the contact layer to the microelectric layer.

5. The manipulator of claim 1, wherein the thermally responsive recess features comprise anisotropically aligned microchannels.

6. The manipulator of claim 5, wherein the anisotropically aligned microchannels are characterized by an average diameter and:
   the thermally actuated geometry has an average contracted diameter ($D_A$);
   the thermally relaxed geometry has an average relaxed diameter ($D_R$); and
   $D_A$ is less than $D_R$, wherein $0.2 \leq D_A/D_R \leq 0.98$.

7. The manipulator of claim 6, wherein the recess features, including $D_A$ and $D_R$, are configured to generate a contact pressure with a manipulated surface that is:
   between 0.1 Pa and 500 Pa per recess feature; and/or
   between 1 kPa and 100 kPa over the entire contact surface in physical contact with the manipulated surface.

8. The manipulator of claim 7, wherein $D_A$ and $D_R$ are selected to generate a contact force with a manipulated surface that is between 0.5 mN and 500 N.

9. The manipulator of claim 7, wherein the manipulated surface is:
   a thin biological tissue;
   an ultrathin electronic film;
   a fragile inorganic film or membrane; or
   a thin semiconductor layer.

10. The manipulator of claim 1, wherein the recess features have, for a thermally relaxed geometry:
    an average lineal density of between 1 and 500 recess features per mm;
    a depth of between 10 µm and 3 cm, including a depth corresponding to a thickness of the capture layer for a microchannel recess feature;
    a characteristic dimension, including a diameter, a length and/or a width, independently selected from between 10 µm and 3 cm; and/or
    a recess feature wall thickness of between 0.1 µm and 10 µm.

11. The manipulator of claim 1, wherein the microelectric heater comprises a flexible pattern of resistive wires embedded in or supported by a polymer layer, and optionally a barrier layer to prevent oxidation of the resistive wires, having a total microelectric heater thickness less than or equal to 50 µm.

12. The manipulator of claim 1, wherein the electrical power source provides an actuation voltage to the microelectric heater of between 0.1 V to 10 V to actuate the microelectric heater and generates an actuated temperature at the contact surface of between 30° C. and 40° C. within 10 seconds of actuation of the electrical power source.

13. The manipulator of claim 1, wherein upon removal of the actuation voltage, the actuated temperature relaxes to a relaxed temperature, including a room temperature or surrounding ambient temperature, within 5 seconds.

14. The manipulator of claim 1, wherein the contact layer has a thermal conductivity of between 0.1° C./mm*s and 0.6° C./mm*s.

15. The manipulator of claim 1, further comprising a support substrate connected to the microelectric heater.

16. A method of handling a transferable layer, the method comprising the steps of:
- providing the manipulator of claim 1;
- energizing the power source to thermally actuate the microelectric heater and provide the thermally responsive recess features in the thermally actuated geometry;
- contacting the contact surface with the transferable layer;
- relaxing the thermally responsive recess features to the thermally relaxed geometry by removing or reducing the energizing step to generate an adhesive pressure in the recess features; and
- lifting and transporting the transferable layer by moving the contact layer of the manipulator, thereby handling the transferable layer.

17. The method of claim 16, further comprising the step of tuning the adhesive pressure to a material property of the transferable layer to reduce risk of damage to the transferable layer.

18. The method of claim 16, wherein the transferable layer is a mechanically fragile ultra-thin layer.

19. The method of claim 16, wherein the transferable layer is a biomaterial comprising living cells or an ultrathin electronic film.

20. The method of any claim 16, further comprising the steps of:
- increasing a temperature of the contact layer to provide the thermally responsive recess features in the thermally actuated state; and
- releasing the transferable layer from the contact surface having the thermally responsive recess features in the thermally actuated state.

* * * * *